(12) United States Patent
Back et al.

(10) Patent No.: US 12,091,408 B2
(45) Date of Patent: Sep. 17, 2024

(54) STORE OVERLOAD-INDUCED CALCIUM RELEASE INHIBITORS AND METHODS FOR PRODUCING AND USING THE SAME

(71) Applicants: Tom Back, Calgary (CA); Wayne Chen, Calgary (CA); Chris Smith, Calgary (CA); Dawei Jiang, Watertown, MA (US); UTI Limited Partnership, Calgary (CA)

(72) Inventors: Tom Back, Calgary (CA); Wayne Chen, Calgary (CA); Chris Smith, Calgary (CA); Dawei Jiang, Watertown, MA (US)

(73) Assignee: UTI Limited Partnership, Calgary (CA)

( * ) Notice: Subject to any disclaimer, the term of this patent is extended or adjusted under 35 U.S.C. 154(b) by 0 days.

(21) Appl. No.: 14/915,368

(22) PCT Filed: Sep. 27, 2014

(86) PCT No.: PCT/US2014/057918
§ 371 (c)(1),
(2) Date: Feb. 29, 2016

(87) PCT Pub. No.: WO2015/031914
PCT Pub. Date: Mar. 5, 2015

(65) Prior Publication Data
US 2016/0214973 A1    Jul. 28, 2016

Related U.S. Application Data

(60) Provisional application No. 61/872,533, filed on Aug. 30, 2013.

(51) Int. Cl.
| | | |
|---|---|---|
| *C07D 419/12* | (2006.01) |
| *C07C 217/28* | (2006.01) |
| *C07C 217/32* | (2006.01) |
| *C07C 217/34* | (2006.01) |
| *C07C 217/38* | (2006.01) |
| *C07C 217/54* | (2006.01) |
| *C07C 217/92* | (2006.01) |
| *C07C 233/20* | (2006.01) |
| *C07D 209/08* | (2006.01) |
| *C07D 209/88* | (2006.01) |
| *C07D 215/227* | (2006.01) |
| *C07D 231/56* | (2006.01) |
| *C07D 235/06* | (2006.01) |
| *C07D 235/08* | (2006.01) |
| *C07D 265/36* | (2006.01) |
| *C07D 279/16* | (2006.01) |
| *C07D 279/20* | (2006.01) |
| *C07D 279/34* | (2006.01) |
| *C07D 281/10* | (2006.01) |

(Continued)

(52) U.S. Cl.
CPC .......... *C07D 419/12* (2013.01); *C07C 217/28* (2013.01); *C07C 217/32* (2013.01); *C07C 217/34* (2013.01); *C07C 217/38* (2013.01); *C07C 217/54* (2013.01); *C07C 217/92* (2013.01); *C07C 233/20* (2013.01); *C07D 209/08* (2013.01); *C07D 209/88* (2013.01); *C07D 215/227* (2013.01); *C07D 231/56* (2013.01); *C07D 235/06* (2013.01); *C07D 235/08* (2013.01); *C07D 265/36* (2013.01); *C07D 279/16* (2013.01); *C07D 279/20* (2013.01); *C07D 279/34* (2013.01); *C07D 281/10* (2013.01); *C07D 401/12* (2013.01); *C07D 405/12* (2013.01); *C07D 413/12* (2013.01); *C07D 417/06* (2013.01); *C07C 2603/18* (2017.05); *C07C 2603/74* (2017.05)

(58) Field of Classification Search
CPC .. C07D 209/88; C07D 209/86; C07D 419/12; C07D 209/08; C07D 215/227; C07D 231/56; C07D 235/06; C07D 235/08; C07D 265/36; C07D 279/16; C07D 279/20; C07D 279/34; C07D 281/10; C07D 401/12; C07D 405/12; C07D 413/12; C07D 417/06; C07C 217/28; C07C 217/32; C07C 217/34; C07C 217/38; C07C 217/54; C07C 217/92; C07C 233/20; C07C 2603/18; C07C 2603/74
USPC ........................................................ 548/442
See application file for complete search history.

(56) References Cited

U.S. PATENT DOCUMENTS

| | | | | |
|---|---|---|---|---|
| 5,137,734 A | * | 8/1992 | Spiegelman | ............ A61K 31/13 424/574 |
| 6,214,854 B1 | * | 4/2001 | Wang | ..................... A61K 31/00 514/411 |

(Continued)

FOREIGN PATENT DOCUMENTS

| | | | | |
|---|---|---|---|---|
| WO | WO 0107409 A1 | * | 2/2001 | ........... C07D 209/88 |
| WO | WO 2015031914 | | 3/2015 | |

OTHER PUBLICATIONS

Zhou et al. Nature Medicine (2011), 17(8), 1003-1009.*

(Continued)

*Primary Examiner* — Sun Jae Yoo
(74) *Attorney, Agent, or Firm* — Remenick PLLC

(57) ABSTRACT

The present invention provides compounds having store overload-induced $Ca^{2+}$ release (SOICR) inhibitory activity and methods for producing and using the same. In particular, compounds of the invention is of the formula: $R^1—X^1-L-X^2—R^2$, wherein $R^1$, $X^1$, L, $X^2$, and $R^2$ are those defined herein.

9 Claims, 7 Drawing Sheets

Figure 1:
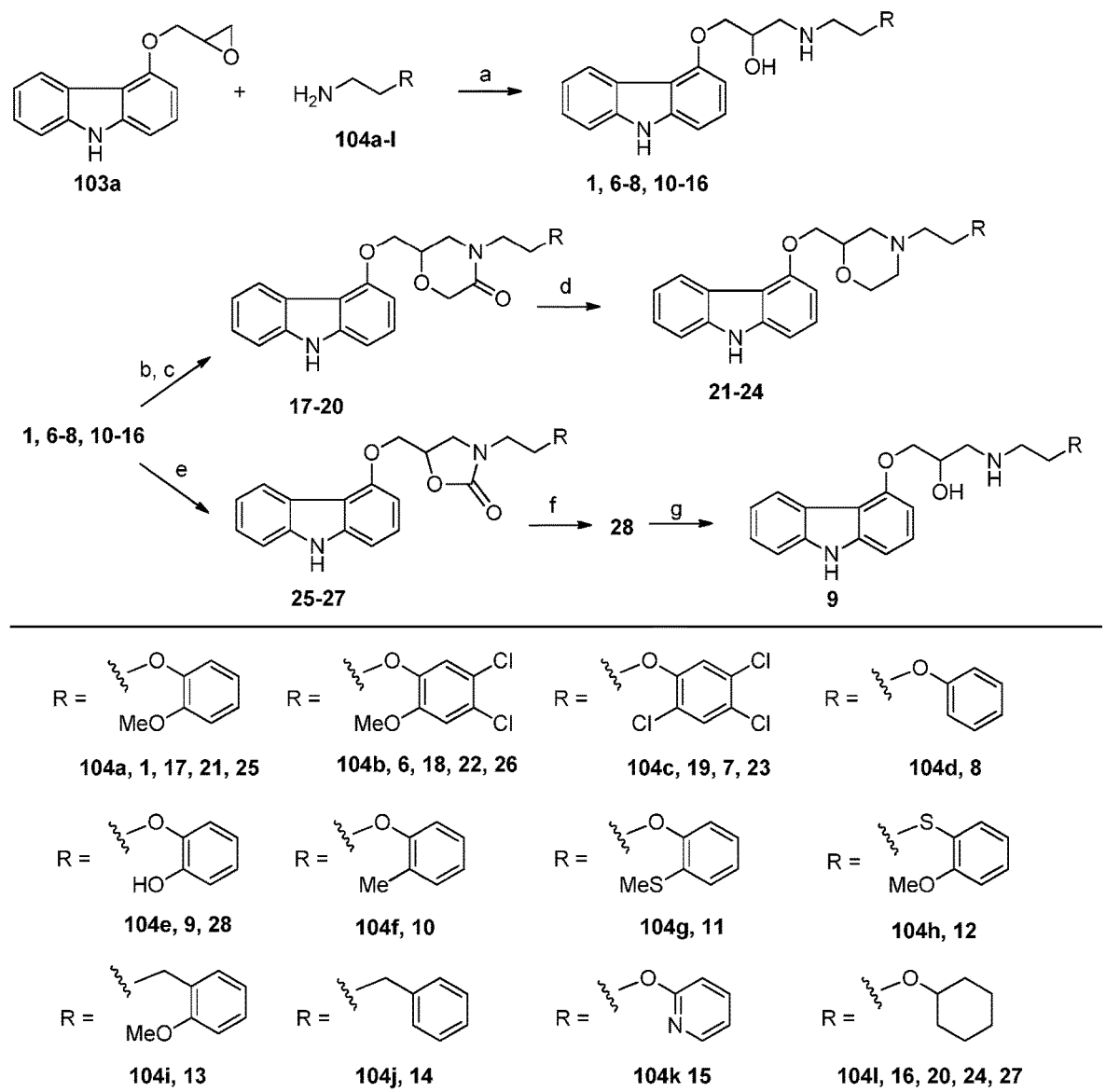

(51) Int. Cl.
*C07D 401/12* (2006.01)
*C07D 405/12* (2006.01)
*C07D 413/12* (2006.01)
*C07D 417/06* (2006.01)

(56) References Cited

U.S. PATENT DOCUMENTS

| | | | | |
|---|---|---|---|---|
| 6,399,631 | B1 | 6/2002 | Elliott et al. | |
| 8,703,804 | B2* | 4/2014 | Chen | C07D 209/82 514/25 |
| 2002/0143045 | A1* | 10/2002 | Hildesheim | C07D 209/88 514/411 |
| 2003/0166702 | A1* | 9/2003 | Kor | C07D 209/88 514/411 |
| 2007/0254849 | A1 | 11/2007 | Chen et al. | |
| 2008/0125476 | A1* | 5/2008 | Ini | C07D 209/88 514/411 |
| 2008/0255134 | A1* | 10/2008 | Taylor | C07D 403/14 514/252.03 |
| 2008/0287688 | A1* | 11/2008 | Sanganbhatla | C07D 209/88 548/444 |
| 2009/0005429 | A1* | 1/2009 | Trepat Guixer | C07D 209/88 514/411 |
| 2010/0076047 | A1* | 3/2010 | Budidet | C07D 209/88 514/411 |
| 2011/0015247 | A1* | 1/2011 | Thota | C07D 209/88 514/411 |
| 2011/0124879 | A1* | 5/2011 | Thaper | C07D 209/88 548/444 |
| 2014/0228409 | A1* | 8/2014 | Yamamoto | A61K 31/403 514/339 |

OTHER PUBLICATIONS

Chen et al., 2007, caplus an 2007:1243217.*
Yuan et al., 2005, caplus an 2005:295804.*
Carbazole, 2018, https://en.wikipedia.org/wiki/Carbazole.*
Wiedemann et al., 1980, caplus an 1980:128716, for RN 72956-07-1.*
Wiedemann et al., 1980, caplus an 1980:128716, for RN 72956-43-5.*
Maier et al., 1996, caplus an 1996:459576.*
Zhou et al., 2011, Nature Medicine, vol. 17, No. 8, 1003-1010.*
International Search Report and Written Opinion for WO Mar. 14-19, 2015, dated 2015031914.
MacLennan et al., Store overload-induced Ca+2 release as a triggering mechanism for CPVT and MH episodes caused by mutations in RYR and CASQ genes. Journal of Physiology, vol. 587(13), pp. 3113-3115, 2009.
Smith et al., Novel Carvedilol Analogs that suppress Store Overload Induced Ca2+ Release. Journal of Medicinal Chemistry, vol. 56(21), pp. 8626-8655 Nov. 14, 2013.
Bundgaard, Design of Prodrugs, pp. 7-9, 21-24, Elsevier, Amsterdam 1985.
Silverman, The Organic Chemistry of Drug Design and Drug Action, pp. 352-401, Academic Press, San Diego, Calif., 1992).

* cited by examiner (a) LiBr, DME, 50 °C or *i*-PrOH, reflux. (b) chloroacetyl chloride, Et$_3$N, CHCl$_3$, room temp. (c) NaH, THF, room temp. (d) LiAlH$_4$, THF, room temp. (e) 1,1'-carbonyldiimidazole, Et$_3$N, CH$_2$Cl$_2$, room temp. (f) BBr$_3$, CH$_2$Cl$_2$, room temp. (g) 2M NaOH, EtOH, reflux.

FIGURE I

(a) MeI, THF, room temp. (b) (MeO)₂C=O, DABCO, DMF, 95 °C. (c) LiOH, EtOH, reflux. (d) i-PrOH, reflux. (e) NaH, MeI, DMF, room temp.

(a) 1 M NaOH, DMSO, room temp. or 40 °C. (b) i-PrOH, reflux.

(a) LiBr, DME, 60 °C. (b) K₂CO₃, DMF, 100 °C. (c) TBAF, THF, room temp. (d) TsCl, Et₃N, CHCl₃, 0 °C. (e) 104a, LiBr, DME, reflux. (f) *i*-PrOH, reflux. (g) LiBr, DME, reflux.

1 M NaOH, DMSO, room temp. or 40 °C. (b) 104a, *i*-PrOH, reflux. (c) 104a, Et₃N, MeOH, 60 °C. (d) EtOH, reflux. (e) 104a, K₂CO₃, cat. KI, EtOH, reflux. (f) TFA, CH₂Cl₂, room temp.

(a) NaH, THF, 0 °C. (b) 104a, LiBr, DME, 60 °C or *i*-PrOH, reflux. (c) 1 M NaOH, DMSO, 40 °C. (d) NH$_2$NH$_2$.H$_2$O, KOH, ethylene glycol, 100-160 °C. (e) Ni$_2$B, MeOH-THF-H$_2$O, room temp.

(a) *i*-PrOH, reflux. (b) BnNH$_2$, *i*-PrOH, reflux. (c) 121, NaBH(OAc)$_3$, 1,2-dichloroethane or 122, DIPEA, cat. KI, MeCN, 60 °C. (d) H$_2$, 10% Pd/C, MeOH. (e) ethyl bromoacetate, NaOH, DMF, room temp. (f) KOH, MeOH-H$_2$O. (g) 104a or 118f, EDC·HCl, HOBT·H$_2$O, Et$_3$N, THF, room temp. (h) DAST, CH$_2$Cl$_2$-THF, -78 °C, 1 h; then K$_2$CO$_3$, room temp., 2 h.

(a) Borax, H₂O, room temp. (b) MeOH, 2 M NaOH, room temp. (c) TFA, TFAA, 60 °C. (d) TMSN₃, TFA, room temp. (e) LiAlH₄, THF-Et₂O, reflux. (f) Formaldehyde, NaBH₃CN, MeOH, room temp.

STORE OVERLOAD-INDUCED CALCIUM RELEASE INHIBITORS AND METHODS FOR PRODUCING AND USING THE SAME

FIELD OF THE INVENTION

The present invention relates to store overload-induced calcium release (SOICR) inhibitors and methods for producing and using the same. In particular, SOICR inhibitors are useful in treating a subject suffering from a cardiac condition associated with $Ca^{2+}$ efflux through the ryanodine receptor type 2 ("RyR2") $Ca^{2+}$ release channel.

BACKGROUND OF THE INVENTION

Heart failure is a progressive and often fatal cardiac condition that is responsible for millions of hospitalizations and over 300,000 deaths in the U.S. and over a million in Western countries annually. Ventricular arrhythmias are one of the leading causes of sudden death, particularly in patients with heart failure. While a variety of antiarrhythmic drug therapies have been evaluated in clinical trials, to date only limited survival benefits have been observed. Antagonists of β-adrenergic receptors (i.e., β-blockers) have been of special interest in these studies, as overstimulation of these receptors can trigger fatal ventricular arrhythmias. It has been shown that in some studies that the underlying mechanism of this process involves an overload of $Ca^{2+}$ in the sarcoplasmic reticulum, which results in spontaneous $Ca^{2+}$ efflux through the ryanodine receptor type 2 ("RyR2") $Ca^{2+}$ release channel. In turn, this store overload-induced calcium release (SOICR) through a defective RyR2 triggers delayed afterdepolarization (DAD), which has been implicated in catecholaminergic polymorphic ventricular tachycardia (CPVT), ventricular tachyarrhythmia and sudden death.

The nonselective β-blocker carvedilol (1) and certain congeners have been shown to also inhibit the α-adrenergic receptor and exhibit antioxidant activity. Thus, 1 has proven effective in suppressing ventricular arrhythmias in patients with failing hearts. Unfortunately, the benefits of carvedilol therapy are limited by drug intolerance and excessive β-blockade, with attendant complications of bradycardia and hypotension. The present inventors have found that a variety of other α- and β-blockers, as well as antioxidants, failed in the suppression of SOICR. Without being bound by any theory, this indicates that the efficacy of carvedilol in suppressing SOICR occurs independently of its α- and β-blocking activity and its antioxidant properties, and is instead principally due to its ability to stabilize $Ca^{2+}$ handling via the RyR2 channel. In fact, the present inventors have previously shown that three novel carvedilol analogs 2-4, with comparable abilities to inhibit SOICR to that of the parent compound 1 (ca. 10 μmolar), but with strongly attenuated β-blockade (ca. μmolar compared to nanomolar for 1) proved highly effective in preventing stress-induced ventricular arrhythmias in mice (vide infra), without the undesired effects of excessive β-blockade.

Therefore, there is a need for compounds that have a potent SOICR-suppressing activity but with diminished α- and β-blockade.

SUMMARY OF THE INVENTION

Carvedilol is an effective drug for the treatment of cardiac arrhythmias in patients with heart failure. This activity is in part due to its ability to inhibit store overload-induced calcium release (SOICR) through the RyR2 channel. Unfortunately, carvedilol is also a strong β-blocker resulting in complications such as bradycardia and hypotension.

Thus, some aspects of the invention provide SOICR inhibitors that have a significantly reduced β-blockade activity, thereby significantly reducing the undesired side-effects associated with carvedilol and other β-blockers. In particular, one aspect of the invention provide a compound of the formula:

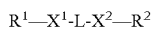  (Compound of Formula I)

where
$R^1$ is selected from the group consisting of carbazolyl; 2,3,4,9-tetrahydro-1H-carbazolyl; 9H-fluorenyl; dibenzo[b,d]furanyl; (phenylamino)phenyl; 10H-phenothiazinyl; naphthalenyl; adamantanyl; (adamantanyl)alkyl; N-acyl-9H-cabazolyl; 10H-5,5-dioxide-phenothiazinyl; 2-oxo-1,2,3,4,4a,8a-hexahydroquinolinyl; 1H-indolyl, and 1H-indazolyl, each of which is optionally substituted;
$X^1$ is O or $NR^3$;
L is a linker having 3 to 9 atoms in the chain with at least two heteroatom substituents in which each of heteroatom is independently selected from the group consisting of O and N, wherein two heteroatoms in the linker optionally form a heterocyclic ring, or a heteroatom of linker L is attached to $R^2$ and together with $X^2$ form a heterocyclic ring, or a heteroatom of linker L and $X^2$ together form a heterocyclic ring;
$X^2$ is alkylene, O, S, or $NR^4$, or when $X^2$ is O, S, or $NR^4$, then $X^2$ together with a substituent in $R^2$ can form a heterocyclic ring;
$R^2$ is selected from the group consisting of phenyl; benzyl; pyridyl; benzo[d]oxazolyl, and benzofuranyl, each of which is optionally substituted; and
each of $R^3$ and $R^4$ is independently selected from the group consisting of: hydrogen; alkyl; and a nitrogen protecting group,
provided
when $R^1$ is optionally substituted carbazol-4yl, then $R^2$ is optionally substituted benzyl or pyridyl; or one of the two heteroatoms in linker L is N, which is located closer to $R^1$ relative to the other heteroatom in linker L; or one of the two heteroatoms in linker L is carbonyl; or a heteroatom of linker L is attached to $R^2$ and together with $X^2$ form a heterocyclic ring;
when $R^1$ is unsubstituted carbazol-3-yl, then linker L has at least 7 atoms in the chain; or two heteroatoms in the linker form a heterocyclic ring; and
when $R^1$ is unsubstituted carbazol-2-yl, then linker L has at least 7 atoms in the chain; or two heteroatoms in the linker form a heterocyclic ring; or $R^2$ is a phenyl substituted with a substituent comprising halide, haloalkyl, or a combination thereof.

It should be appreciated that compound of Formula I does not include carvedilol.

Other aspects of the invention provide a pharmaceutical composition comprising a compound of the invention and a method for using and producing the same.

Yet another aspect of the invention provides, a method of treating cardiac arrhythmia in a heart failure patient, said method comprising administering to a heart failure patient a therapeutically effective amount of a Compound of Formula I to treat cardiac arrhythmia. In some embodiments, said Compound of Formula I inhibits store-overload-induced calcium release (SOICR). Within these embodiments, in some instances SOICR inhibition by Compound of Formula I is achieved by regulating calcium efflux through the RyR2 channel Yet in other embodiments, calcium ion-induced calcium ion release (CICR) by Compound of Formula I is minimally inhibited or not inhibited. As used herein, the term "minimally inhibited" when referring to CICR inhibition refers to having $IC_{50}$ of CICR inhibition of about 100 µM or more, typically 500 µM or more, and often 1000 µM or more.

Still another aspect of the invention provides a pharmaceutical composition comprising a Compound of Formula I, or a pharmaceutically acceptable salt or a prodrug thereof.

BRIEF DESCRIPTION OF THE INVENTION

FIGS. 1-8 are reaction schemes for synthesizing various compounds of the invention.

DETAILED DESCRIPTION OF THE INVENTION

Definition

"Carbazol-n-yl" refers to a carbazolyl moiety that is attached to a linker ("L") at the n-position of the carbazole ring system. Thus, for example, carbazol-3-yl refers to a structure of the formula:

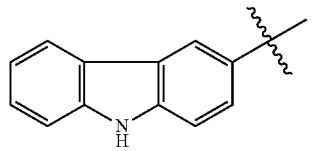 [SMILES: *c1ccc2[nH]c3ccccc3c2c1]

where the linker is attached to the 3-position of the carbazole, as indicated by the wavy line. Carbazole can be optionally substituted with 1 to 4 substituents, typically one or two substituents, each of which is independently selected. Suitable substituents for a carbazole include, but are not limited to, halide, alkyl, and haloalkyl.

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Linker" refers to a group of atoms that is covalently bonded to $X^1$ and $X^2$ of Compound of Formula I. A linker is generally comprised of an alkylene group that has at least two heteroatoms such as O and/or N substituents. Typically, at least one of the heteroatom substituent forms a part of the chain of atoms in the linker. Thus, a linker often comprises a hydrocarbon moiety with at least one heteroatom in the linking chain. In some cases, two or more heteroatoms in the linker can form a heterocycle within the linking chain. The number of atoms in a linker refers to the smallest number of chain atoms that links $X^1$ and $X^2$.

The terms "heterocycle," "heterocyclyl" and "heterocyclic ring" are used interchangeably herein and refer to a non-aromatic mono- or bi-cyclic moiety of three to twelve, typically three to six, ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclic ring can be optionally substituted independently with one or more, typically one, two, or three, substituents. When two or more substituents are present in a heterocyclic ring, each substituent is independently selected. Exemplary substituents for heterocyclic ring that are useful in the present invention include, but are not limited to, alkyl, haloalkyl, and halo.

"Alkylene" refers to a saturated linear divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to a pharmacologically substantially inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, *Design of Prodrugs, pp.* 7-9, 21-24, Elsevier, Amsterdam 1985 and Silverman, *The Organic Chemistry of Drug Design and Drug Action*, pp. 352-401, Academic Press, San Diego, Calif., 1992). Prodrugs commonly known in the art include acid derivatives that are well known to one skilled in the art, such as, but not limited to, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability. For example, a compound of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of a compound of the invention through the carbonyl carbon prodrug sidechain. Other examples of prodrugs include, but are not limited to, esters (e.g., acetate, formate, and benzoate derivatives), carbamates (e.g., N,N-dimethylaminocarbonyl) of hydroxy functional groups in Compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Some aspects of the invention provide synthesis, characterization and bioassay of compounds having SOICR inhibitory activity. In one particular embodiment, some compounds of the invention are based on the carvedilol structural motif and identification of features that correlate with SOICR inhibitory activity. Some aspects of the invention are based on one or more structure modifications of carvedilol (1) as shown below.

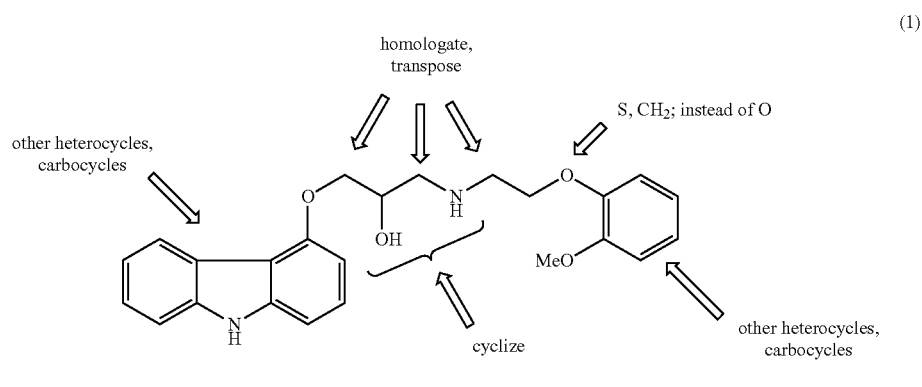

(1)

Carvedilol

In particular, one aspect of the invention provides a compound of the formula:

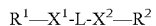 (Compound of Formula I)

where $R^1$ is selected from the group consisting of carbazolyl; 2,3,4,9-tetrahydro-1H-carbazolyl; 9H-fluorenyl; dibenzo[b,d]furanyl; (phenylamino)phenyl; 10H-phenothiazinyl; naphthalenyl; adamantanyl; (adamantanyl)alkyl; N-acyl-9H-cabazolyl; 10H-5,5-dioxide-phenothiazinyl; 2-oxo-1,2,3,4,4a,8a-hexahydroquinolinyl; 1H-indolyl, and 1H-indazolyl, each of which is optionally substituted; $X^1$ is O or $NR^3$; L is a linker having 3 to 9 atoms in the chain with at least two heteroatom substituents in which each of heteroatom is independently selected from the group consisting of O and N, wherein two heteroatoms in the linker optionally form a heterocyclic ring, or a heteroatom of linker L is attached to $R^2$ and together with $X^2$ form a heterocyclic ring, or a heteroatom of linker L and $X^2$ together form a heterocyclic ring; $X^2$ is alkylene, O, S, or $NR^4$, or when $X^2$ is O, S, or $NR^4$, then $X^2$ together with a substituent in $R^2$ can form a heterocyclic ring; $R^2$ is selected from the group consisting of phenyl; benzyl; pyridyl; benzo[d]oxazolyl, and benzofuranyl, each of which is optionally substituted; and each of $R^3$ and $R^4$ is independently selected from the group consisting of hydrogen; alkyl, and a nitrogen protecting group, provided
  when $R^1$ is optionally substituted carbazol-4yl, then $R^2$ is optionally substituted benzyl or pyridyl; or one of the two heteroatoms in linker L is N, which is located closer to $R^1$ relative to the other heteroatom in linker L; or one of the two heteroatoms in linker L is carbonyl; or a heteroatom of linker L is attached to $R^2$ and together with $X^2$ form a heterocyclic ring;
  when $R^1$ is unsubstituted carbazol-3-yl, then linker L has at least 7 atoms in the chain; or two heteroatoms in the linker form a heterocyclic ring; and
  when $R^1$ is unsubstituted carbazol-2-yl, then linker L has at least 7 atoms in the chain; or two heteroatoms in the linker form a heterocyclic ring; or $R^2$ is benzo[d]oxazolyl, benzofuranyl, or phenyl substituted with a substituent comprising halide, haloalkyl, or a combination thereof.

In one embodiment, $R^1$ is selected from the group consisting of carbazol-2-yl; carbazol-3-yl; carbazol-4-yl; 2,3,4,9-tetrahydro-1H-carbazol-6-yl; 9H-fluoren-4-yl; 9H-fluoren-9-on-4-yl; dibenzo[b,d]furan-2-yl; (phenylamino)phenyl; 10H-phenothiazin-2-yl; naphthalenyl; adamantanyl; (adamantanyl)alkyl; N-acyl-9H-cabazol-4-yl; 10H-5,5-dioxide-phenothiazin-2-yl; 2-oxo-1,2,3,4,4a,8a-hexahydroquinolin-6-yl; 1H-indol-5-yl, and 1H-indazol-6-yl. each of which is optionally substituted. Within this embodiment, in some instances (adamantanyl)alkyl is (adamantanyl)methyl. Generally, when $R^1$ is substituted, it is substituted with one or two halide. Often each of the halide substituent is independently fluoro or bromo.

Still in another embodiments, $X^1$ is O or NH.

Yet in other embodiments, L is selected from the group consisting of:

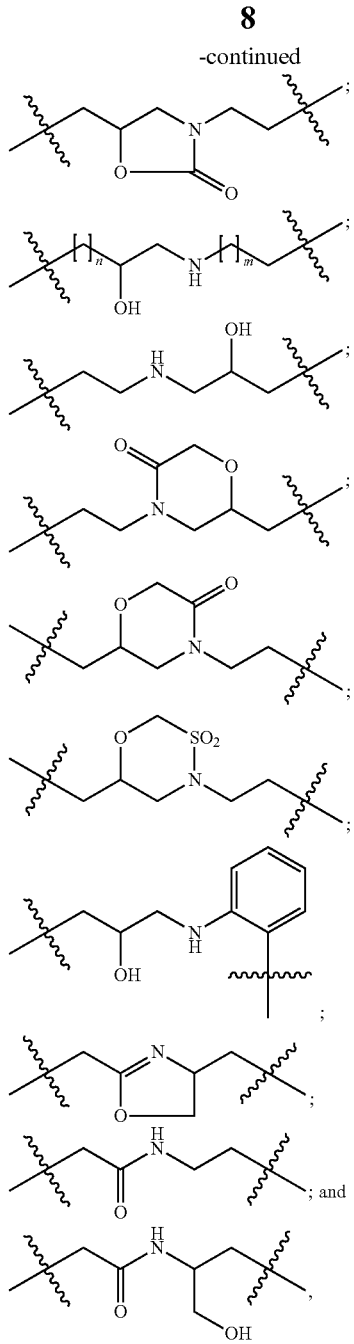

where each of m and x is 1 or 2; and n is 1 to 4.

In another embodiment, a heteroatom of linker L and $X^2$ together form a heterocyclic ring of the formula:

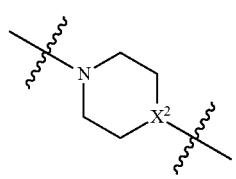

Still yet in another embodiment, a heteroatom of linker L is attached to $R^2$ and together with $X^2$ form a heterocyclic ring of the formula:

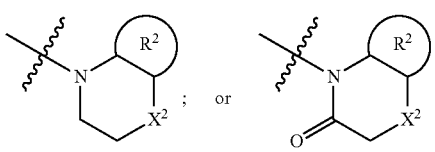

Yet in another embodiment, $R^2$ is selected from the group consisting of phenyl, benzyl, pyrid-2-yl, benzo[d]oxazol-2-yl, and benzofuran-2-yl, each of which is optionally substituted.

Still further, combinations of different embodiments for various groups described herein form other embodiments. In this manner, a variety of compounds are embodied within the present invention.

Another embodiment of the invention provides compounds listed in Tables 1-9.

To determine SOICR inhibitory activity, a single cell bioassay was employed based on the RyR2-R4496C mutant HEK-293 cell line[7,8], in which calcium release from the endoplasmic reticulum through the defective channel was measured by monitoring the fluorescence of a calcium-sensitive indicator dye (fura 2/AM, Invitrogen). $IC_{50}$ values were measured for each of the compounds investigated. As can be seen above, some compounds of the invention include modifications to one or more of the three general subunits of the carvedilol molecule, e.g., the carbazole moiety, catechol moiety, and the linker chain.

Alterations to the carbazole subunit included N-alkylation and acylation, fluorination as well as its replacement by a variety of other nitrogen heterocycles and nonpolar hydrocarbons. Similarly, removal or replacement of the catechol ether groups by sulfur, halogens or alkyl groups was performed, as well as the installation of a variety of heterocycles in their place. The linker chain was subjected to alkylation or cyclization of the β-amino alcohol functionality, as well as homologation and transposition of functional groups. The results indicate that significant alterations are tolerated in each of the three subunits, including ones to hydrogen-bonding groups that are required for the powerful (nanomolar) β-blocking activity exhibited by carvedilol. This β-blocking activity is associated with side effects of carvedilol such as bradycardia and hypotension. Compounds of the invention have a significantly improved SOICR-inhibiting activity compared to carvedilol.

The R4496C mutation in mice renders them highly susceptible to stress-induced ventricular arrhythmias, which are easily triggered by stimulants such as caffeine and epinephrine, thereby providing a useful animal model for evaluating potential antiarrhythmic drugs.[9-14] Thus, one skilled in the art can readily determine in vivo activity using R4496C mutant mice.

Discovery of compounds 2-4 by the present inventors were guided by the x-ray crystal structure of the complex of the carvedilol analog carazolol (5) with the β-adrenergic receptor that had been previously reported by Stevens, Kobilka and their coworkers. Their results indicated that the carbazole amino group participates in hydrogen-bonding with residue S203 of the receptor, while multiple hydrogen bonds occur between the secondary alcohol and the protonated amino group of the β-amino alcohol moiety with residues D113, Y316 and N312. Furthermore, a series of hydrophobic interactions were observed involving the aromatic rings of the carbazole and the N-isopropyl group of 5 with corresponding hydrophobic pockets in the receptor. Without being bound by any theory, blocking, modifying or relocating the corresponding key hydrogen bonding functionalities of carvedilol, as well as by modifying the hydrophobic regions of these molecules, it is believed that binding to the β-adrenergic receptor can be achieved while retaining their desired interaction with RyR2. Similarly, a catechol moiety is a common structural motif in many α-blockers, suggesting that manipulation of this moiety in 1 could result in diminished α-blockade, while leaving RyR2 binding intact.

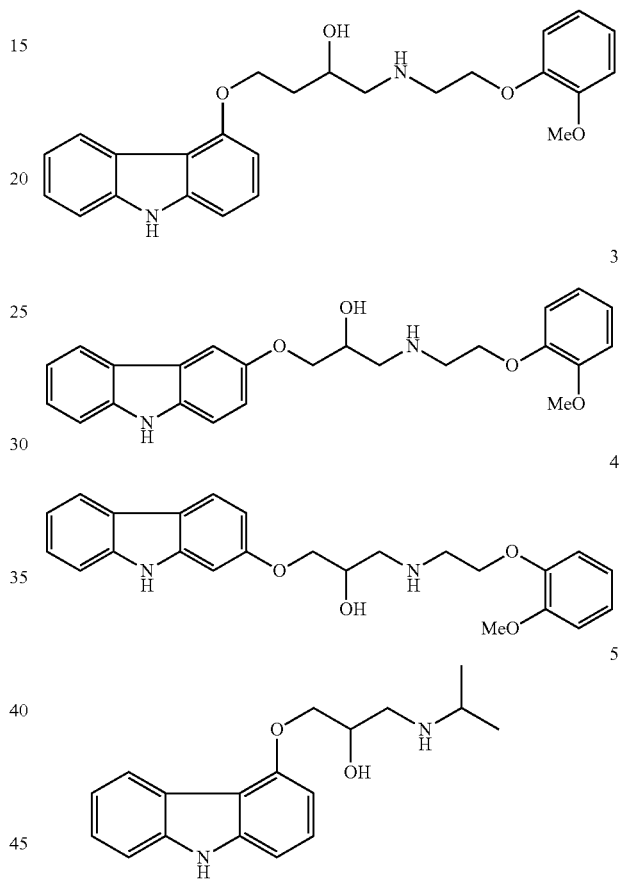

In addition to the carvedilol analogues 2-4, a wide range of compounds were prepared in an attempt to identify compounds that retain the potent SOICR-suppressing activity with diminished α- and β-blockade.

The SOICR inhibitory activity of some compounds of the invention is shown in Tables 1-8, along with that of carvedilol (1) and of several other reference compounds that are included for comparison. All compounds were tested for SOICR inhibition in the RyR2-R4496C mutant HEK293 cell line and the $IC_{50}$ values. As a reference, compound 1 (carvedilol) had an $IC_{50}$ of 15.9 μM (Table 1, entry 1) in this assay. Compounds (6-16) with modified catechol groups are exemplified in Table 1. Aromatic hydroxylation of the catechol moiety of carvedilol at the 4'- and 5'-positions is known to afford phenolic metabolites with strong β-blocking activity. Modification of these sites to probe their effect on SOICR inhibition was therefore of particular interest (entries 2-4, Table 1).

TABLE 1
SOICR inhibition modified catechol analogs of 1.
| entry | compound | Structure | IC$_{50}$ (μM) ± SEM |
|---|---|---|---|
| 1 | carvedilol 1 | 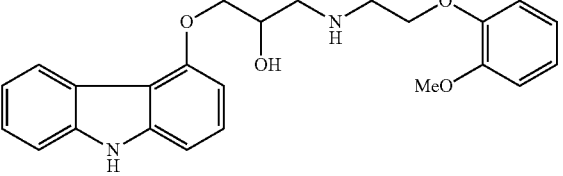 | 15.9 ± 2.5 |
| 2 | 6 | 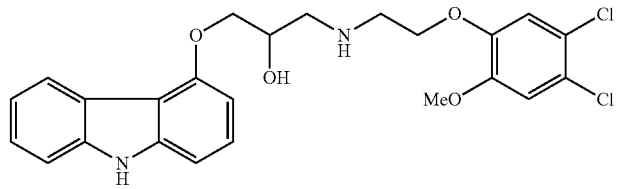 [SMILES: COc1cc(Cl)c(Cl)cc1OCCNCC(O)COc1cccc2[nH]c3ccccc3c12] | 11.2 ± 1.2 |
| 3 | 7 | 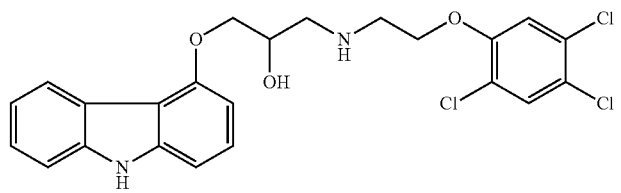 [SMILES: OC(CNCCOc1cc(Cl)c(Cl)cc1Cl)COc1cccc2[nH]c3ccccc3c12] | 28.0 ± 0.63 |
| 4 | 8 | 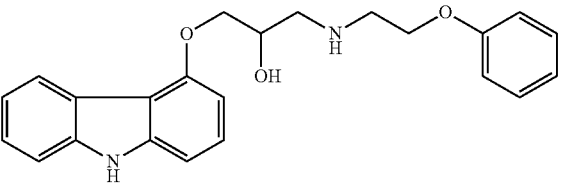 [SMILES: OC(CNCCOc1ccccc1)COc1cccc2[nH]c3ccccc3c12] | 16.8. ± 2.7 |
| 5 | 9 | 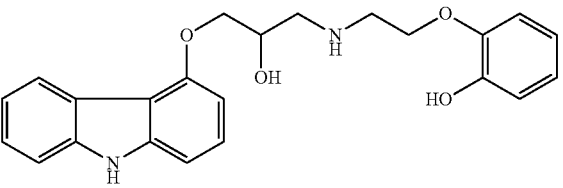 [SMILES: Oc1ccccc1OCCNCC(O)COc1cccc2[nH]c3ccccc3c12] | 7.62 ± 0.44 |
| 6 | 10 | 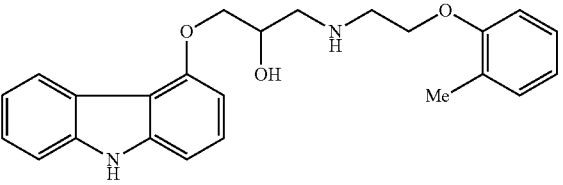 [SMILES: Cc1ccccc1OCCNCC(O)COc1cccc2[nH]c3ccccc3c12] | 15.1 ± 3.7 |
| 7 | 11 | 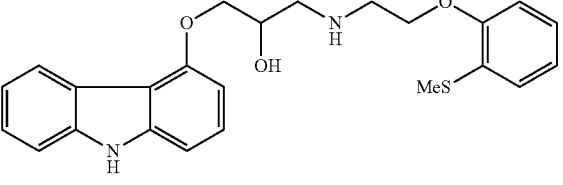 [SMILES: COc1ccccc1CCCNCC(O)COc1cccc2[nH]c3ccccc3c12] | 16.4 ± 4.2 |

TABLE 1-continued

SOICR inhibition modified catechol analogs of 1.

| entry | compound | Structure | IC$_{50}$ (µM) ± SEM |
|---|---|---|---|
| 8 | 12 | (carbazol-4-yloxy)-CH$_2$-CH(OH)-CH$_2$-NH-CH$_2$CH$_2$-S-(2-MeO-phenyl) | 11.6 ± 0.92 |
| 9 | 13 | (carbazol-4-yloxy)-CH$_2$-CH(OH)-CH$_2$-NH-CH$_2$CH$_2$CH$_2$-(2-MeO-phenyl) | 7.43 ± 0.65 |
| 10 | 14 | (carbazol-4-yloxy)-CH$_2$-CH(OH)-CH$_2$-NH-CH$_2$CH$_2$-phenyl | 8.52 ± 1.3 |
| 11 | 15 | (carbazol-4-yloxy)-CH$_2$-CH(OH)-CH$_2$-NH-CH$_2$CH$_2$-O-(2-pyridyl) | 54.9 ± 5.7 |
| 12 | 16 | (carbazol-4-yloxy)-CH$_2$-CH(OH)-CH$_2$-NH-CH$_2$CH$_2$-O-cyclohexyl | 35.2 ± 2.2 |

SOICR inhibitory activity of compounds with modified β-amino alcohol moiety in the linker chain was also investigated. Without being bound by any theory, it is believed that β-amino acid moiety plays a critical role in the excessive β-blockade observed in carvedilol. Entries 1-12 in Table 2 show the IC$_{50}$ values for analogs where this functionality was incorporated into various rings, with or without the previous modifications to the catechol region of the carvedilol molecule given in Table 1. Surprisingly and unexpectedly, exhaustive alkylation of both nitrogens and of the secondary alcohol group in 31 produced a more strongly SOICR-inhibiting compound than either 29 or 30.

TABLE 2

SOICR inhibition by compounds with cyclized or alkylated linker chains.

| entry | compound | structure | IC$_{50}$ (µM) ± SEM |
|---|---|---|---|
| 1 | 17 | morpholinone-based carbazol-4-yloxy analog with 2-MeO-phenoxyethyl | 26.1 ± 3.6 |

TABLE 2-continued
SOICR inhibition by compounds with cyclized or alkylated linker chains.
| entry | compound | structure | IC$_{50}$ (μM) ± SEM |
|---|---|---|---|
| 2 | 18 | 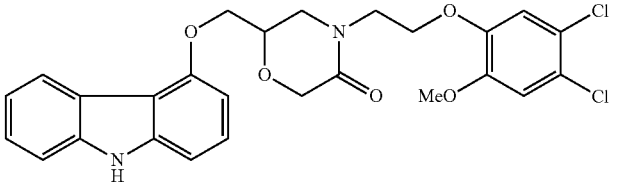 [SMILES: COc1cc(Cl)c(Cl)cc1OCCN1CC(COc2cccc3[nH]c4ccccc4c23)OCC1=O] | >1000 |
| 3 | 19 | 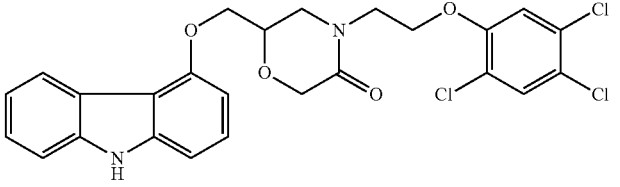 [SMILES: O=C1COC(COc2cccc3[nH]c4ccccc4c23)CN1CCOc1cc(Cl)c(Cl)cc1Cl] | >1000 |
| 4 | 20 | 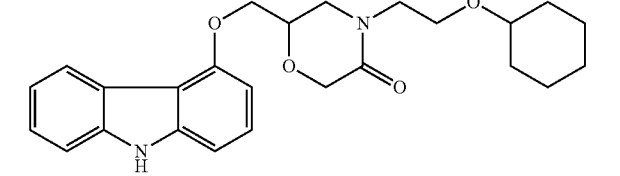 | 52.9 ± 15 |
| 5 | 21 | 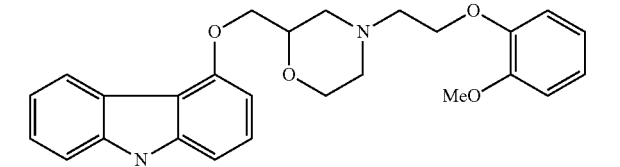 | 22.9 ± 2.7 |
| 6 | 22 | 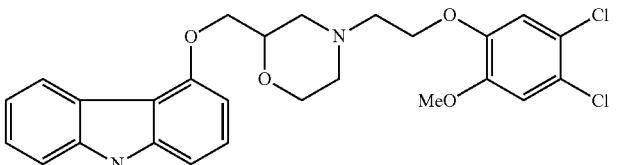 | 86.7 ± 36 |
| 7 | 23 | 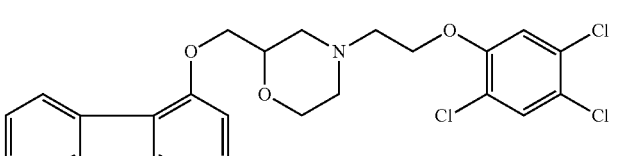 | 364 ± 91 |
| 8 | 24 | 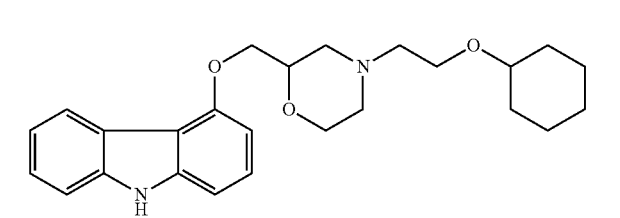 [SMILES: c1ccc2c(c1)[nH]c1cccc(OCC3CN(CCOC4CCCCC4)CCO3)c12] | >1000 |

TABLE 2-continued

SOICR inhibition by compounds with cyclized or alkylated linker chains.

| entry | compound | structure | IC$_{50}$ (μM) ± SEM |
|---|---|---|---|
| 9 | 25 | 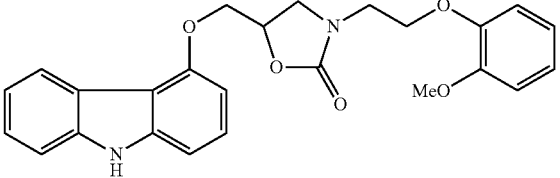 [SMILES: COc1ccccc1OCCN1CC(COc2cccc3[nH]c4ccccc4c23)OC1=O] | 86.3 ± 52 |
| 10 | 26 | 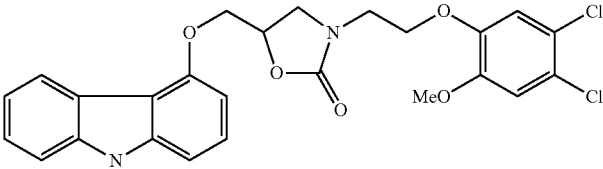 | 97.2 ± 63 |
| 11 | 27 | 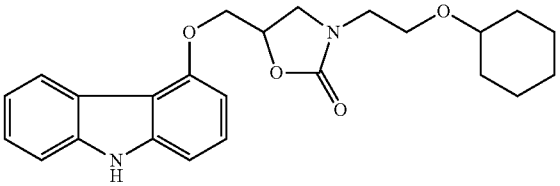 [SMILES: O=C1OC(COc2cccc3[nH]c4ccccc4c23)CN1CCOC1CCCCC1] | 113 ± 25 |
| 12 | 28 | 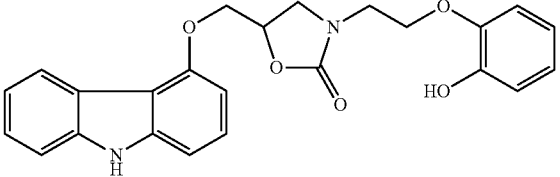 [SMILES: O=C1OC(COc2cccc3[nH]c4ccccc4c23)CN1CCOc1ccccc1O] | 16.1 ± 7.2 |
| 13 | 29 | 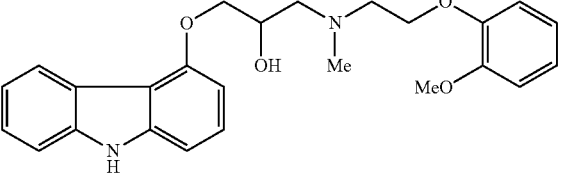 | 18.3 ± 0.01 |
| 14 | 30 | 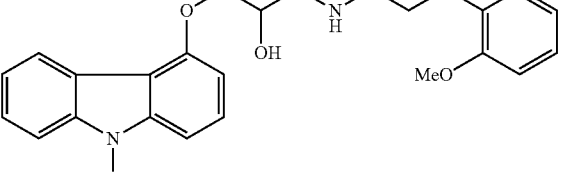 | 35.2 ± 5.2 |
| 15 | 31 | 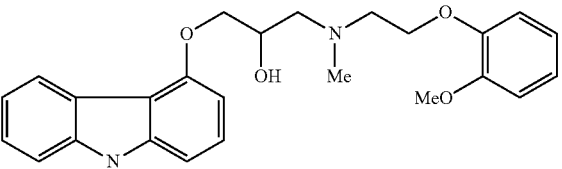 | 11.7 ± 0.65 |

Attempts to determine the effects of homologation of the linker chain at various sites upon SOICR inhibition were also made, as such changes would be expected to disrupt the cooperative hydrogen-bonding of the amino alcohol functionalities to the β-receptor and thus decrease the excessive β-blockade of 1 (Table 3, entries 1-8). Homologation was effected by insertion of one or more extra methylene units between the carbazole ether and secondary alcohol of 1 to afford 2, its cyclized derivative 32, and 33, respectively. Similarly, homologation between the alcohol and amino group provided 34 and the corresponding lactam 35, while insertion of an extra methylene unit between the amino group and the catechol ether and between the catechol ether and aromatic ring afforded derivatives 36 and 37, respectively. Activity of some of these compounds is shown in Table 3.

TABLE 3

Effects of homologation and transposition of linker chain on SOICR inhibition.

| entry | compound | structure | IC$_{50}$ (μM) ± SEM |
|---|---|---|---|
| 1 | 2 | 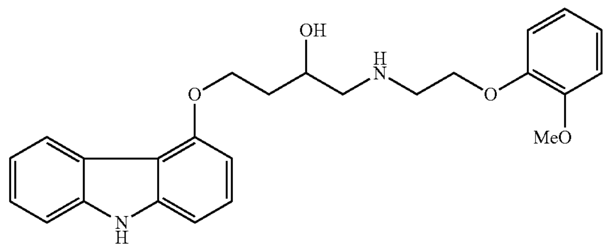 [SMILES: COc1ccccc1OCCNCC(O)CCOc1cccc2[nH]c3ccccc3c12] | 16.8 ± 3.3 |
| 2 | 32 | 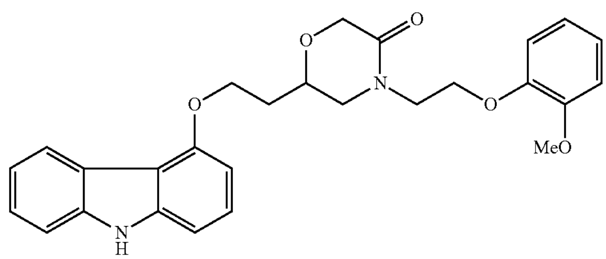 [SMILES: COc1ccccc1OCCN1CC(CCOc2cccc3[nH]c4ccccc4c23)OCC1=O] | 14.6 ± 3.5 |
| 3 | 33 | 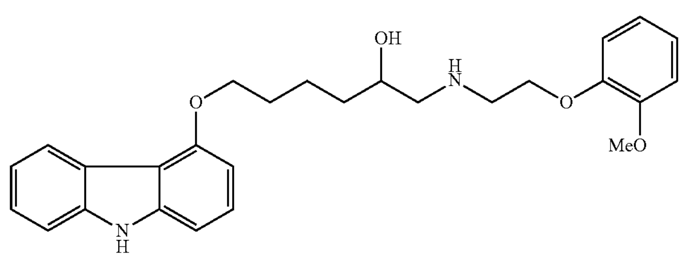 [SMILES: COc1ccccc1OCCNCC(O)CCCCOc1cccc2[nH]c3ccccc3c12] | 11.4 ± 0.75 |
| 4 | 34 | 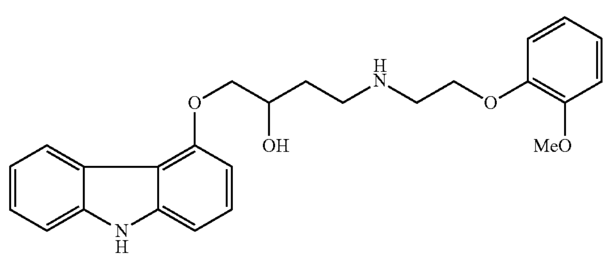 [SMILES: COc1ccccc1OCCNCCC(O)COc1cccc2[nH]c3ccccc3c12] | 13.5 ± 2.3 |
| 5 | 35 | 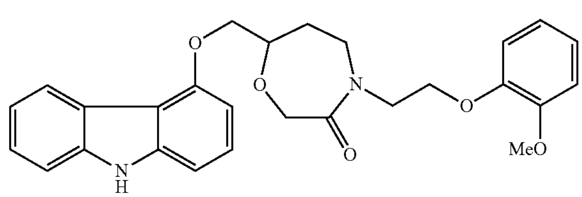 [SMILES: COc1ccccc1OCCN1CCC(COc2cccc3[nH]c4ccccc4c23)OCC1=O] | 86.7 ± 53 |

TABLE 3-continued

Effects of homologation and transposition of linker chain on SOICR inhibition.

| entry | compound | structure | IC$_{50}$ (µM) ± SEM |
|---|---|---|---|
| 6 | 36 | 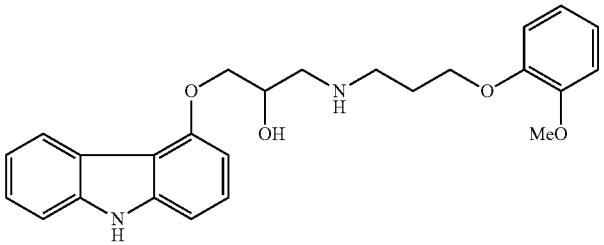 | 20.0 ± 1.6 |
| 7 | 37 | 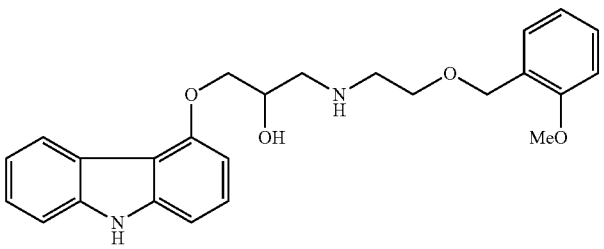 | 10.2 ± 0.49 |
| 8 | 38 | 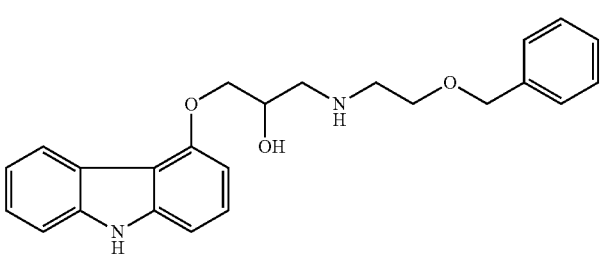 | 9.51 ± 2.3 |
| 9 | 39 | 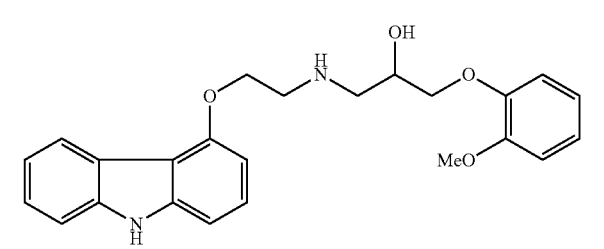 | 24.4 ± 3.1 |
| 10 | 40 | 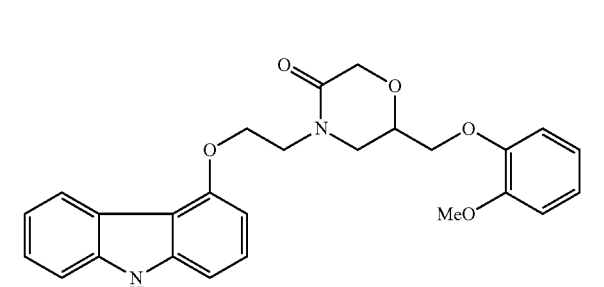 | 26.7 ± 3.2 |

When the point of attachment of the linker was moved from the 4-position of the carbazole moiety (as in carvedilol) to the 3-position, a series of highly active compounds was obtained (Table 4, entries 1-7). Thus, compounds 3, 41, 43 and 44 all proved superior to carvedilol in their inhibition of SOICR. Cyclization of 3 to afford lactam 41 retained the high activity of the parent amino alcohol. Furthermore, homologation of 3 by one, two or three methylene units between the carbazole and hydroxyl functions produced the highly active analogs 43-45, respectively, with the lowest IC$_{50}$ of 4.66 µmol observed for the doubly homologated derivative 44. Single homologation between the alcohol and amino functions in 46 also produced a more potent product than carvedilol.

TABLE 4

SOICR inhibition by 3-carbazolyl analogs.

| entry | compound | structure | IC$_{50}$ (μM) ± SEM |
|---|---|---|---|
| 1 | 3 | 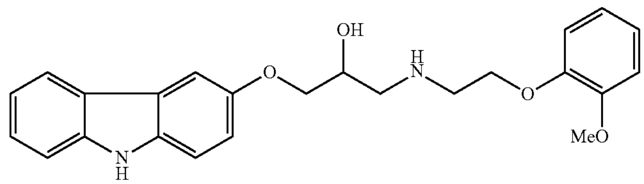 [SMILES: COc1ccccc1OCCNCC(O)COc1ccc2[nH]c3ccccc3c2c1] | 7.74 ± 1.1 |
| 2 | 41 | 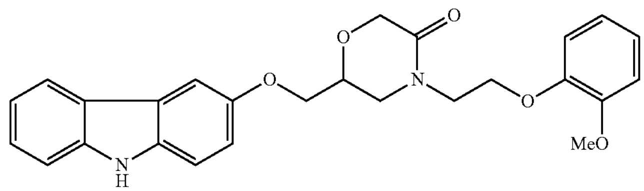 [SMILES: COc1ccccc1OCCN1CC(COc2ccc3[nH]c4ccccc4c3c2)OCC1=O] | 6.20 ± 1.8 |
| 3 | 42 | 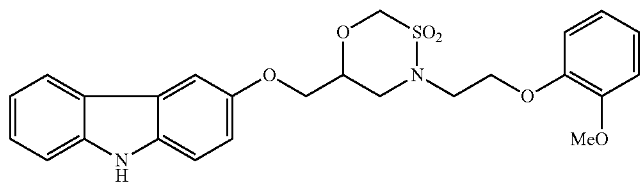 [SMILES: COc1ccccc1OCCN1CC(COc2ccc3[nH]c4ccccc4c3c2)OCS1(=O)=O] | 436 ± 330 |
| 4 | 43 | 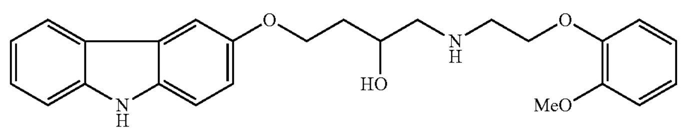 [SMILES: COc1ccccc1OCCNCC(O)CCOc1ccc2[nH]c3ccccc3c2c1] | 9.72 ± 3.1 |
| 5 | 44 | 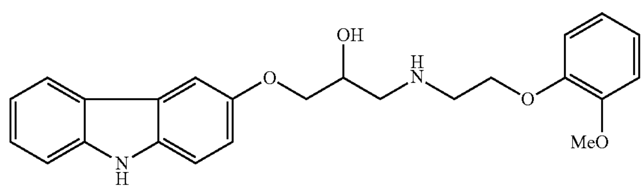 [SMILES: COc1ccccc1OCCNCC(O)COc1ccc2[nH]c3ccccc3c2c1] | 4.66 ± 0.13 |
| 6 | 45 | 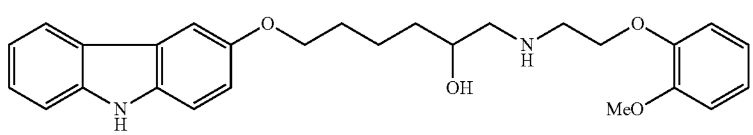 [SMILES: COc1ccccc1OCCNCC(O)CCCCOc1ccc2[nH]c3ccccc3c2c1] | 15.9 ± 5.1 |
| 7 | 46 | 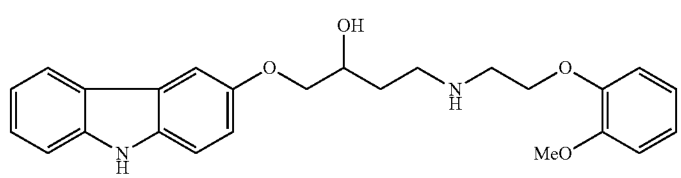 [SMILES: COc1ccccc1OCCNCCC(O)COc1ccc2[nH]c3ccccc3c2c1] | 9.74 ± 2.8 |
| 8 | 47 | 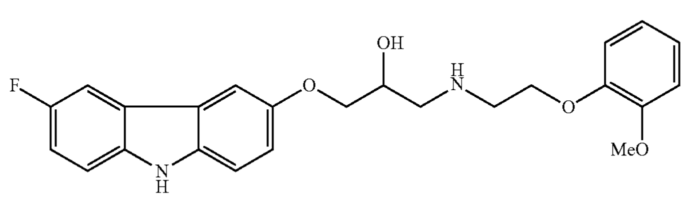 [SMILES: COc1ccccc1OCCNCC(O)COc1ccc2[nH]c3ccc(F)cc3c2c1] | 6.26 ± 2.8 |

TABLE 4-continued

SOICR inhibition by 3-carbazolyl analogs.

| entry | compound | structure | IC$_{50}$ (μM) ± SEM |
|---|---|---|---|
| 9 | 48 | 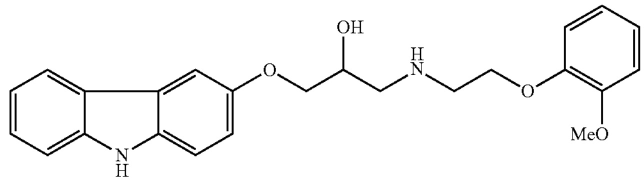 [SMILES: COc1ccccc1OCCNCC(O)COc1ccc2[nH]c3ccccc3c2c1] | 16.6 ± 4.3 |

The 2-substituted carbazole series (Table 5, entries 1-10) was also investigated as well as attachment of the linker chain to the 1-position of the carbazole unit (entry 11, compound 58). The results of in vitro activity are shown in Table 5.

TABLE 5

SOICR inhibition by 2- and 1-carbazolyl analogs.

| entry | compound | structure | IC$_{50}$ (μM) ± SEM |
|---|---|---|---|
| 1 | 4 | 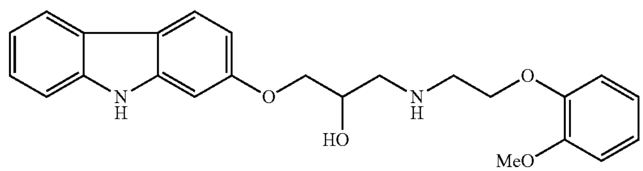 [SMILES: COc1ccccc1OCCNCC(O)COc1ccc2c(c1)[nH]c1ccccc12] | 17.8 ± 3.6 |
| 2 | 49 | 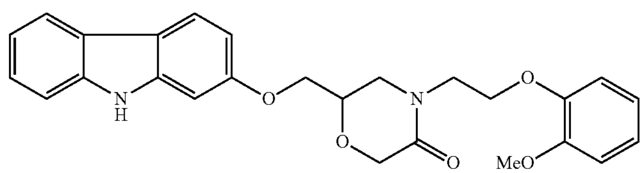 [SMILES: COc1ccccc1OCCN1CC(COc2ccc3c(c2)[nH]c2ccccc23)OCC1=O] | 19.8 ± 1.6 |
| 3 | 50 | 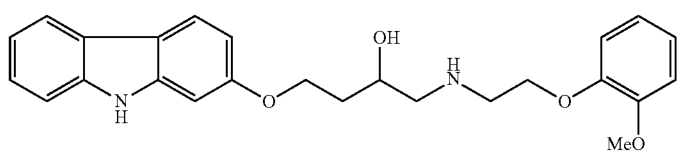 [SMILES: COc1ccccc1OCCNCC(O)CCOc1ccc2c(c1)[nH]c1ccccc12] | 14.6 ± 2.4 |
| 4 | 51 | 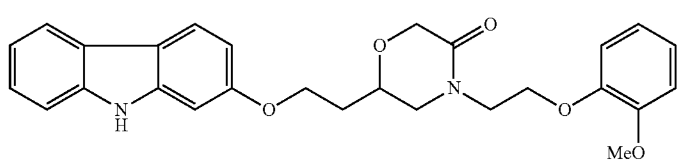 [SMILES: COc1ccccc1OCCN1CC(CCOc2ccc3c(c2)[nH]c2ccccc23)OCC1=O] | >1000 |
| 5 | 52 | 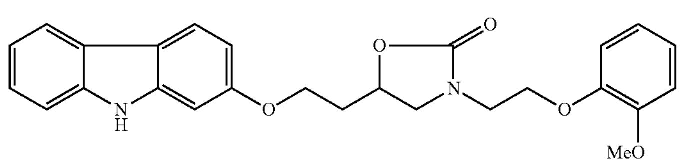 [SMILES: COc1ccccc1OCCN1CC(CCOc2ccc3c(c2)[nH]c2ccccc23)OC1=O] | 354 ± 101 |
| 6 | 53 | 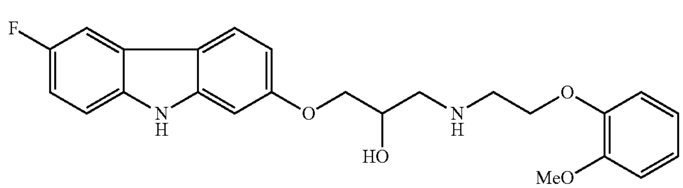 [SMILES: COc1ccccc1OCCNCC(O)COc1ccc2c(c1)[nH]c1ccc(F)cc12] | 5.50 ± 2.3 |

TABLE 5-continued

SOICR inhibition by 2- and 1-carbazolyl analogs.

| entry | compound | structure | IC$_{50}$ (μM) ± SEM |
|---|---|---|---|
| 7 | 54 | 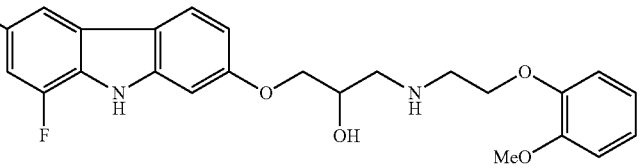 | 4.37 ± 0.49 |
| 8 | 55 | 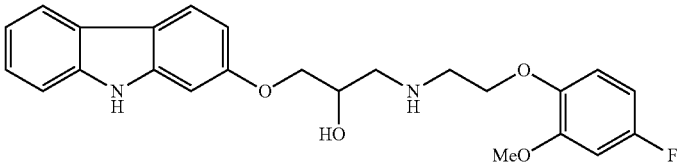 [SMILES: COc1cc(F)ccc1OCCNCC(O)COc1ccc2c(c1)[nH]c1ccccc12] | 10.2 ± 0.86 |
| 9 | 56 | 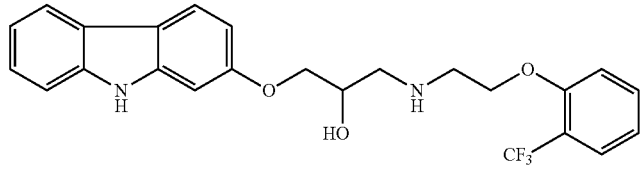 [SMILES: OC(CNCCOc1ccccc1C(F)(F)F)COc1ccc2c(c1)[nH]c1ccccc12] | 15.4 ± 4.6 |
| 10 | 57 | 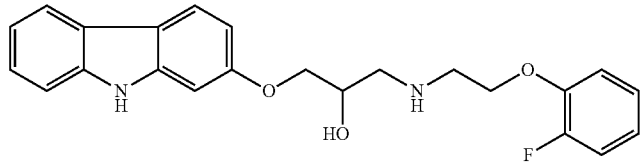 [SMILES: OC(CNCCOc1ccccc1F)COc1ccc2c(c1)[nH]c1ccccc12] | 20.1 ± 4.5 |
| 11 | 58 | 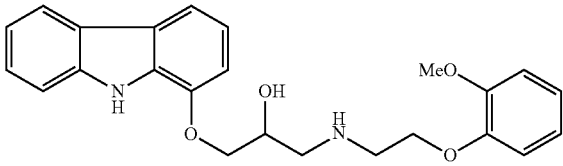 [SMILES: COc1ccccc1OCCNCC(O)COc1cccc2c1[nH]c1ccccc12] | 12.4 ± 1.3 |

It has been suggested that the carbazole moiety of carvedilol serves to embed the molecule in the lipid bilayer of cell membranes. Furthermore, it provides a hydrophobic region and a hydrogen-bonding functionality that are key for binding to the β-adrenergic receptor. In order to determine whether these structural features are also required for SOICR inhibition, a variety of analogs containing modified carbazole units were prepared and assayed (Table 6). As can be seen, replacement of the carbazole with naphthyl residues in 68 and its homologated analog 69 afforded potent SOICR inhibitors.

TABLE 6

Effect of carbazole modification or replacement on SOICR inhibition.

| entry | compound | structure | IC$_{50}$ (μM) ± SEM |
|---|---|---|---|
| 1 | 59 | 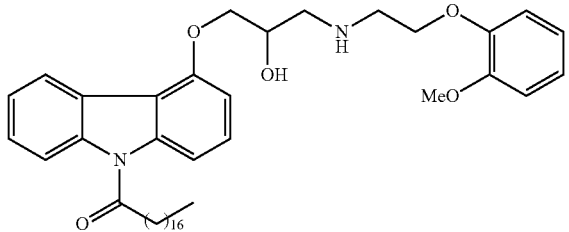 | >1000 |

TABLE 6-continued

Effect of carbazole modification or replacement on SOICR inhibition.

| entry | compound | structure | IC$_{50}$ (μM) ± SEM |
|---|---|---|---|
| 2 | 60 | 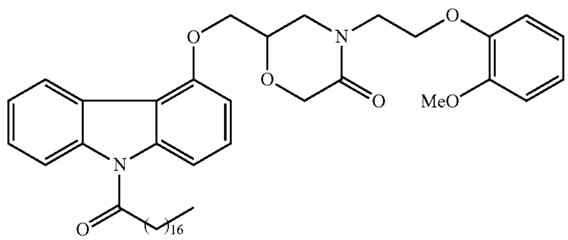 | 86.5 ± 20 |
| 3 | 61 | 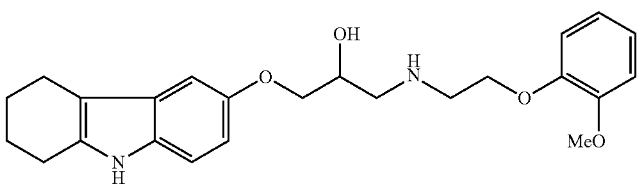 [SMILES: COc1ccccc1OCCNCC(O)COc1ccc2[nH]c3c(c2c1)CCCC3] | 17.4 ± 1.1 |
| 4 | 62 | 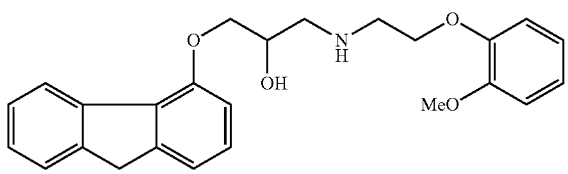 [SMILES: COc1ccccc1OCCNCC(O)COc1cccc2c1-c1ccccc1C2] | 17.0 ± 1.6 |
| 5 | 63 | 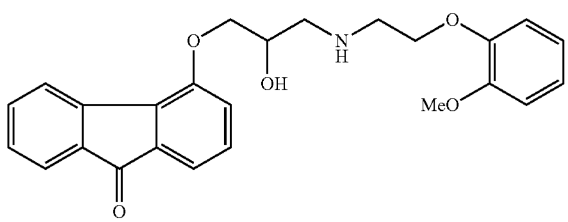 [SMILES: COc1ccccc1OCCNCC(O)COc1cccc2c1-c1ccccc1C2=O] | 30.1 ± 2.6 |
| 6 | 64 | 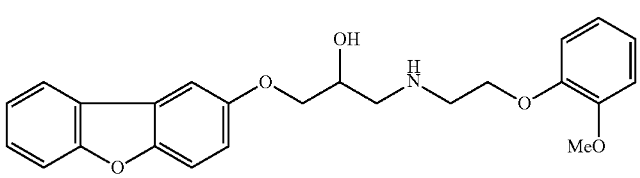 [SMILES: COc1ccccc1OCCNCC(O)COc1ccc2oc3ccccc3c2c1] | 11.0 ± 1.6 |
| 7 | 65 | 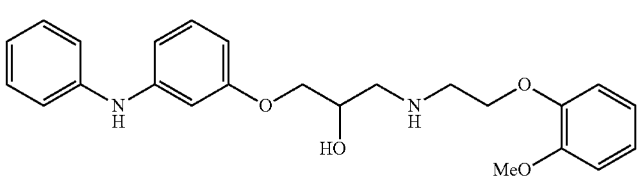 [SMILES: COc1ccccc1OCCNCC(O)COc1cccc(Nc2ccccc2)c1] | 18.2 ± 2.7 |
| 8 | 66 | 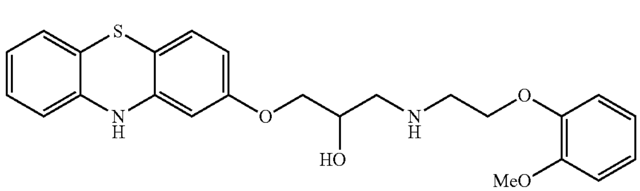 [SMILES: COc1ccccc1OCCNCC(O)COc1ccc2c(c1)Nc1ccccc1S2] | 5.7 ± 2.7 |

TABLE 6-continued

Effect of carbazole modification or replacement on SOICR inhibition.

| entry | compound | structure | IC$_{50}$ (µM) ± SEM |
|---|---|---|---|
| 9 | 67 | 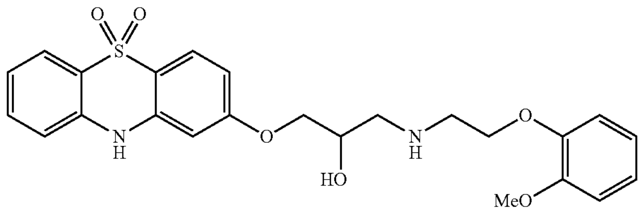 [SMILES: COc1ccccc1OCCNCC(O)COc1ccc2c(c1)Nc1ccccc1S2(=O)=O] | 65.8 ± 6.5 |
| 10 | 68 | 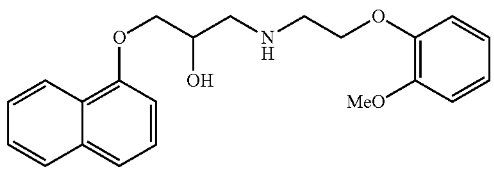 [SMILES: COc1ccccc1OCCNCC(O)COc1cccc2ccccc12] | 15.1 ± 1.2 |
| 11 | 69 | 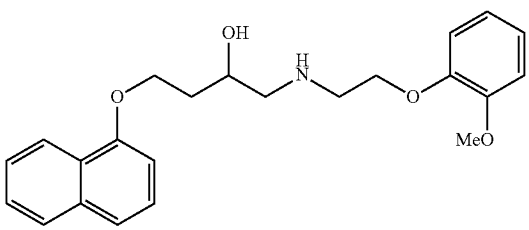 [SMILES: COc1ccccc1OCCNCC(O)CCOc1cccc2ccccc12] | 9.77 ± 2.0 |
| 12 | 70 | 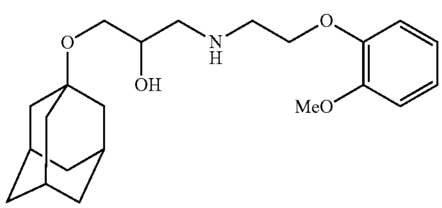 [SMILES: COc1ccccc1OCCNCC(O)COC12CC3CC(CC(C3)C1)C2] | 75.6 ± 20 |
| 13 | 71 | 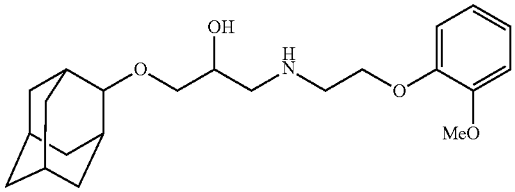 [SMILES: COc1ccccc1OCCNCC(O)COC1C2CC3CC(C2)CC1C3] | 29.7 ± 11 |
| 14 | 72 | 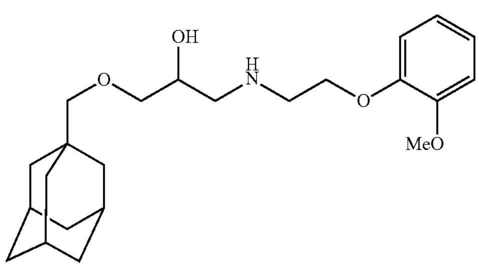 [SMILES: COc1ccccc1OCCNCC(O)COCC12CC3CC(CC(C3)C1)C2] | 28.0 ± 3.1 |
| 15 | 73 | 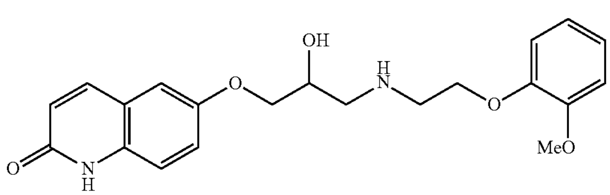 [SMILES: COc1ccccc1OCCNCC(O)COc1ccc2[nH]c(=O)ccc2c1] | >1000 |

TABLE 6-continued

Effect of carbazole modification or replacement on SOICR inhibition.

| entry | compound | structure | IC$_{50}$ (μM) ± SEM |
|---|---|---|---|
| 16 | 74 | 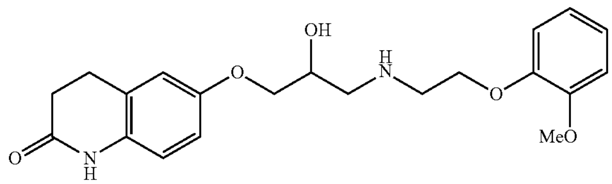 [SMILES: COc1ccccc1OCCNCC(O)COc1ccc2c(c1)CCC(=O)N2] | 463 ± 129 |
| 17 | 75 | 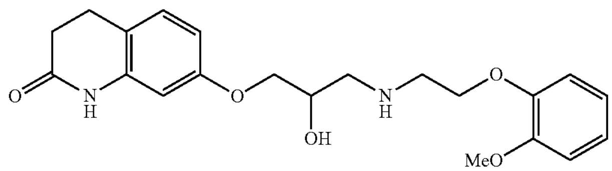 [SMILES: COc1ccccc1OCCNCC(O)COc1ccc2c(c1)NC(=O)CC2] | >1000 |
| 18 | 76 | 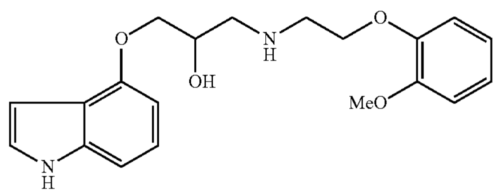 [SMILES: COc1ccccc1OCCNCC(O)COc1cccc2[nH]ccc12] | 213 ± 29 |
| 19 | 77 | 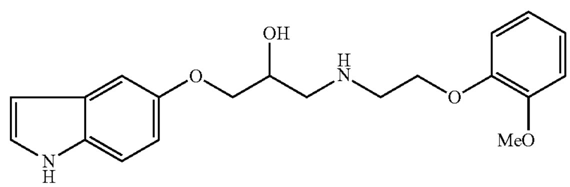 [SMILES: COc1ccccc1OCCNCC(O)COc1ccc2[nH]ccc2c1] | 101 ± 16 |
| 20 | 78 | 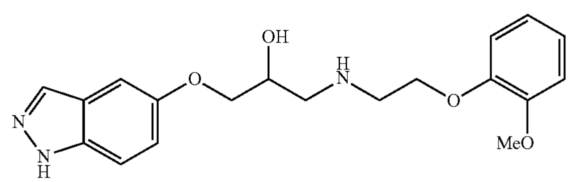 [SMILES: COc1ccccc1OCCNCC(O)COc1ccc2[nH]ncc2c1] | >1000 |
| 21 | 79 | 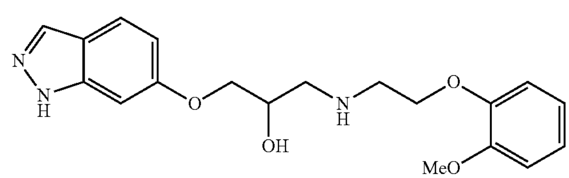 [SMILES: COc1ccccc1OCCNCC(O)COc1ccc2cn[nH]c2c1] | 545 ± 213 |
| 22 | 80 | 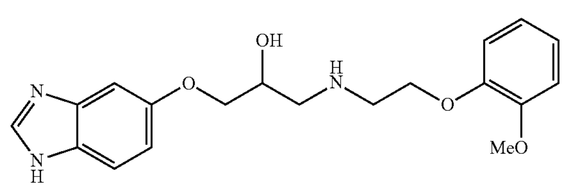 [SMILES: COc1ccccc1OCCNCC(O)COc1ccc2[nH]cnc2c1] | >1000 |

Compounds of the invention also include those having a heterocyclic group in the linker chain or in place of the catechol moiety (Table 7, entries 1-12), as well as compounds with amide instead of amino alcohol functionalities (Table 7, entries 13-14). As can be seen, benzomorpholine 83 proved more than twice as potent as carvedilol (1). Surprisingly and unexpectedly, replacement of the amino alcohol moiety of 1 with amide linkages in 93 and 94 afforded the most potent SOICR inhibitors investigated, with IC$_{50}$ values of ca. 3.6 compared with 15.9 for carvedilol.

TABLE 7

Other modified carvedilol derivatives as SOICR inhibitors

| entry | compound | structure | IC$_{50}$ (μM) ± SEM |
|---|---|---|---|
| 1 | 81 | 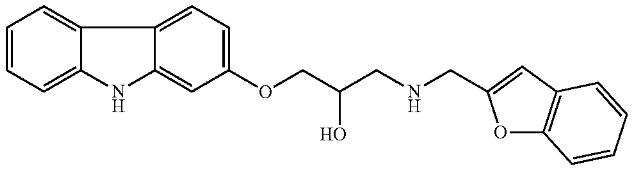 [SMILES: OC(CNCc1cc2ccccc2o1)COc1ccc2c(c1)[nH]c1ccccc12] | >1000 |
| 2 | 82 | 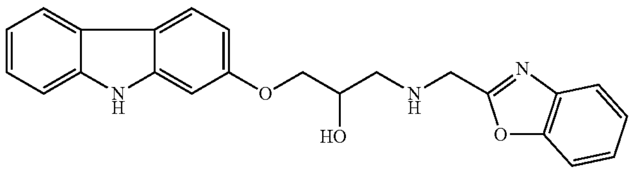 [SMILES: OC(CNCc1nc2ccccc2o1)COc1ccc2c(c1)[nH]c1ccccc12] | >1000 |
| 3 | 83 | 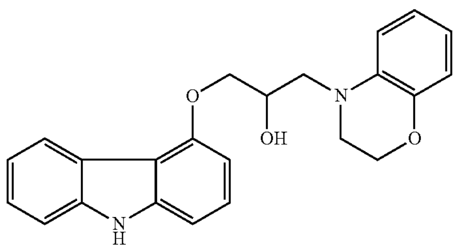 [SMILES: OC(COc1cccc2[nH]c3ccccc3c12)CN1CCOc2ccccc21] | 5.76 ± 1.3 |
| 4 | 84 | 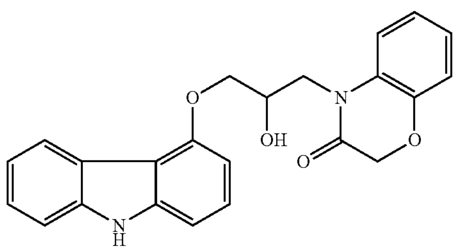 [SMILES: O=C1COc2ccccc2N1CC(O)COc1cccc2[nH]c3ccccc3c12] | 15.8 ± 5.0 |
| 5 | 85 | 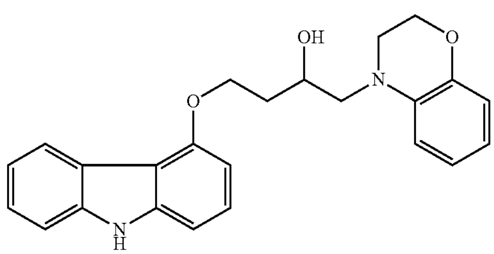 [SMILES: OC(CCOc1cccc2[nH]c3ccccc3c12)CN1CCOc2ccccc21] | 19.7 ± 9.0 |
| 6 | 86 | 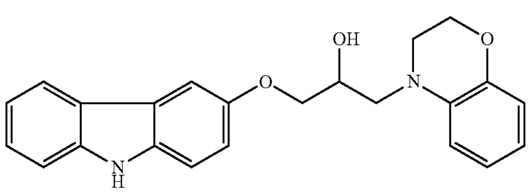 [SMILES: OC(COc1ccc2[nH]c3ccccc3c2c1)CN1CCOc2ccccc21] | 8.61 ± 0.47 |
| 7 | 87 | 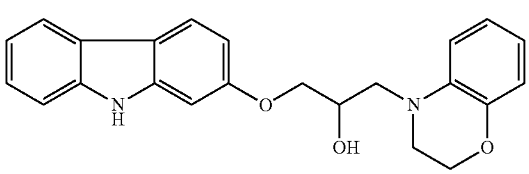 [SMILES: OC(COc1ccc2c(c1)[nH]c1ccccc12)CN1CCOc2ccccc21] | >1000 |

TABLE 7-continued

Other modified carvedilol derivatives as SOICR inhibitors

| entry | compound | structure | IC$_{50}$ (μM) ± SEM |
|---|---|---|---|
| 8 | 88 | 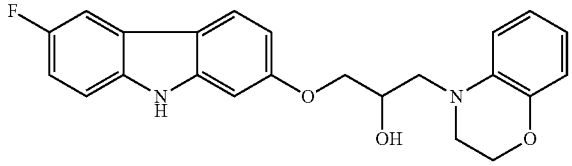 [SMILES: OC(COc1ccc2c(c1)[nH]c1ccc(F)cc12)CN1CCOc2ccccc21] | >1000 |
| 9 | 89 | 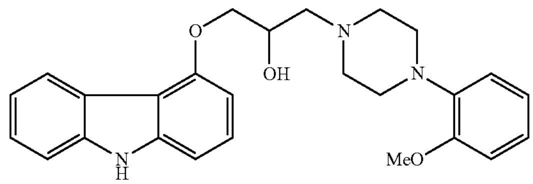 [SMILES: COc1ccccc1N1CCN(CC(O)COc2cccc3[nH]c4ccccc4c23)CC1] | 34.9 ± 3.7 |
| 10 | 90 | 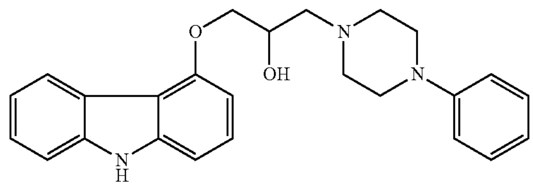 [SMILES: OC(COc1cccc2[nH]c3ccccc3c12)CN1CCN(c2ccccc2)CC1] | 62.7 ± 15 |
| 11 | 91 | 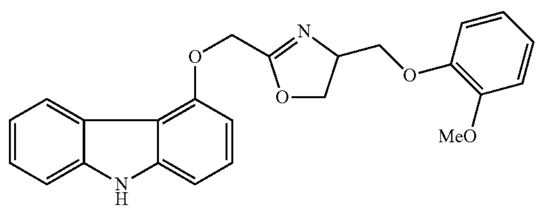 [SMILES: COc1ccccc1OCC1COC(COc2cccc3[nH]c4ccccc4c23)=N1] | 19.8 ± 1.7 |
| 12 | 92 | 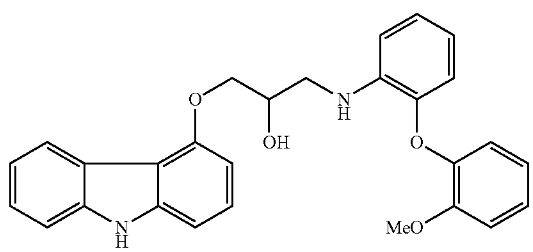 [SMILES: COc1ccccc1Oc1ccccc1NCC(O)COc1cccc2[nH]c3ccccc3c12] | 94.5 ± 60 |
| 13 | 93 | 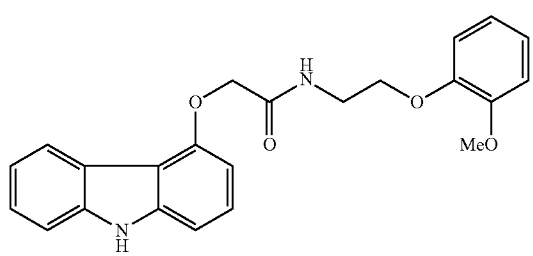 [SMILES: COc1ccccc1OCCNC(=O)COc1cccc2[nH]c3ccccc3c12] | 3.55 ± 0.30 |
| 14 | 94 | 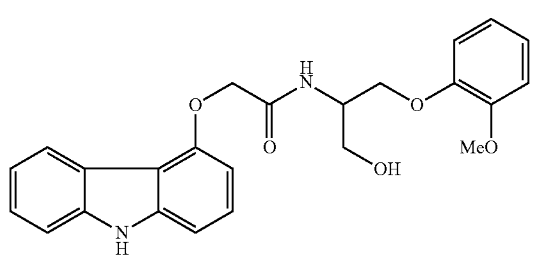 [SMILES: COc1ccccc1OCC(CO)NC(=O)COc1cccc2[nH]c3ccccc3c12] | 3.63 ± 0.18 |

Several other classes of compounds have been reported to provide salutary effects in the treatment of cardiac arrhythmias. SOICR inhibiting properties of some of these compounds were measured to compare them with the above carvedilol analogs. See Table 8. The clinically useful β-blocker metoprolol (95) showed no noticeable SOICR inhibitory activity in the mutant HEK293 single cell bioassay. The former result is consistent with the present inventors' previous finding that carvedilol is unique in the family of β-blocker drugs in effectively suppressing SOICR in the HEK293 cell line and in the knock-in mouse model.

Compound 96 has been reported to inhibit $Ca^{2+}$-induced $Ca^{2+}$ release (CICR) in skeletal muscle sarcoplasmic reticulum. In the RyR2-R4496C mutant HEK293 cell assay, it exhibited negligible activity, which improved substantially when its structure was incorporated into the novel carvedilol derivative 97. The thiazepinone compounds S107 (99) and JTV519 (102) have been reported to suppress ventricular arrhythmias and sudden death in mice through enhanced binding of the 12.6 kDa FK506 binding protein (FKBP12.6) to the RyR2 channel. However, neither S107, its hydrochloride salt 100, nor its isomer 101 displayed any measurable activity in the present assay. On the other hand, the amide derivative 102 showed some SOICR inhibitory activity.

TABLE 8

SOICR inhibition by other types of antiarrhythmic agents

| entry | compound | structure | $IC_{50}$ (μM) ± SEM |
|---|---|---|---|
| 1 | metoprolol 95 | 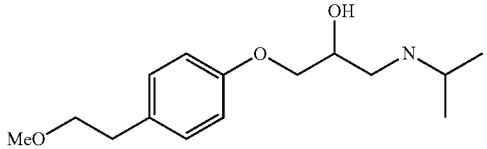 [SMILES: COCCc1ccc(OCC(O)CNC(C)C)cc1] | >1000 |
| 3 | 96 | 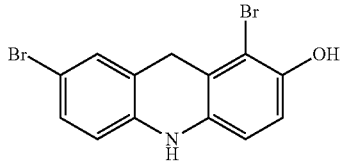 [SMILES: Oc1ccc2c(c1Br)Cc1cc(Br)ccc1N2] | >1000 |
| 4 | 97 | 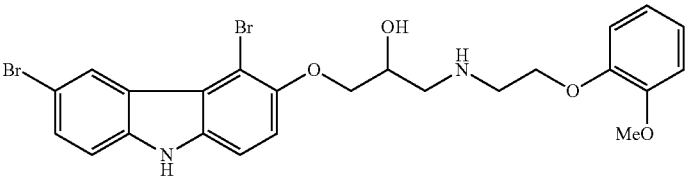 [SMILES: COc1ccccc1OCCNCC(O)COc1ccc2[nH]c3ccc(Br)cc3c2c1Br] | 69.8 ± 33 |
| 5 | 98 | 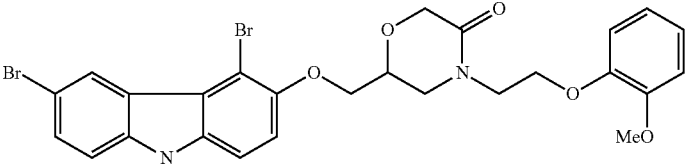 | >1000 |
| 6 | 99 | 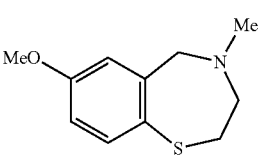 [SMILES: COc1ccc2c(c1)CN(C)CCS2] | >1000 |
| 7 | 100 | 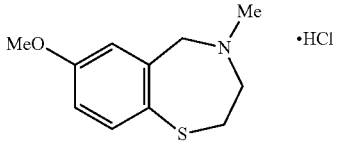 [SMILES: COc1ccc2c(c1)CN(C)CCS2 ; Cl] | >1000 |
| 8 | 101 | 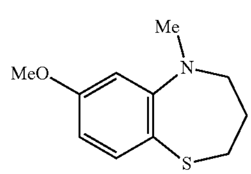 [SMILES: COc1ccc2c(c1)N(C)CCCS2] | >1000 |

TABLE 8-continued
SOICR inhibition by other types of antiarrhythmic agents
| entry | compound | structure | IC$_{50}$ (μM) ± SEM |
|---|---|---|---|
| 9 | 102 | 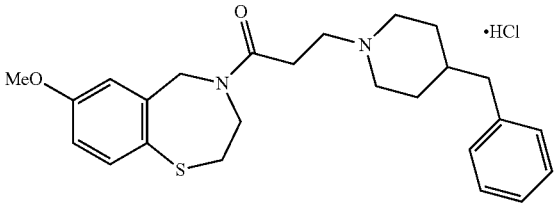 [SMILES: COc1ccc2c(c1)CN(C(=O)CCN1CCC(Cc3ccccc3)CC1)CCS2 ; Cl] | 34.3 ± 6.7 |
Other specific examples of compounds of the invention include those shown in Table 9 below:
TABLE 9
Other exemplary compounds of the invention
| | | |
|---|---|---|
| CS-X-77 | 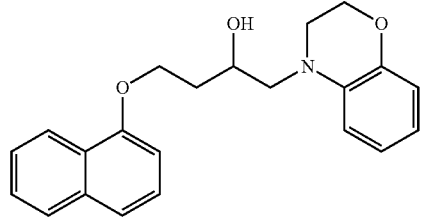 [SMILES: OC(CCOc1cccc2ccccc12)CN1CCOc2ccccc21] | 102.83 ± 73.35 |
| CS-X-73 | 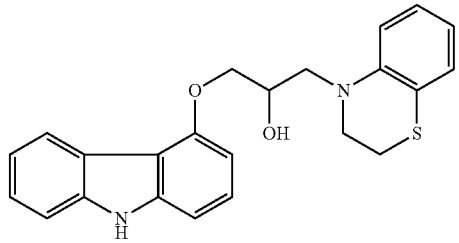 [SMILES: OC(COc1cccc2[nH]c3ccccc3c12)CN1CCSc2ccccc21] | 48.01 ± 22.16 |
| CS-X-30 | 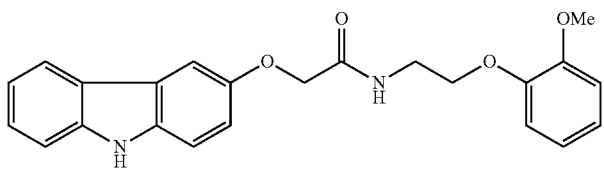 [SMILES: COc1ccccc1OCCNC(=O)COc1ccc2[nH]c3ccccc3c2c1] | 10.06 ± 0.26 |
| CS-X-32 | 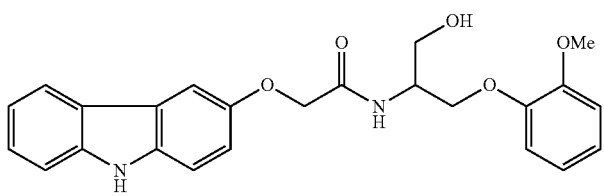 [SMILES: COc1ccccc1OCC(CO)NC(=O)COc1ccc2[nH]c3ccccc3c2c1] | 4.37 ± 0.45 |
| CS-X-27 | 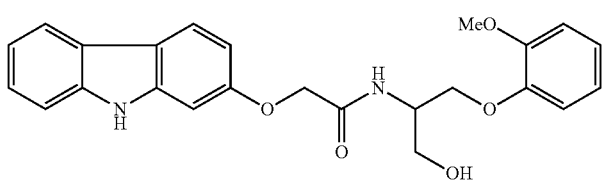 [SMILES: COc1ccccc1OCC(CO)NC(=O)COc1ccc2c(c1)[nH]c1ccccc12] | 15.46 ± 2.44 |

TABLE 9-continued
Other exemplary compounds of the invention
| | | |
|---|---|---|
| VK-I-153 | 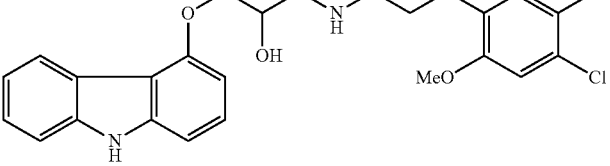 | 11.22 ± 1.15 |
| CS-X-93 | 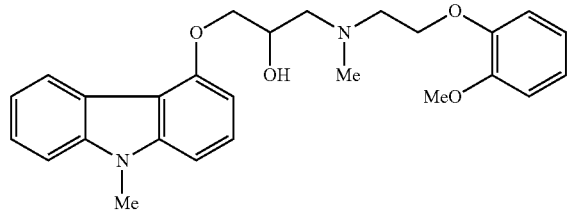 [SMILES: COc1ccccc1OCCN(C)CC(O)COc1cccc2c1c1ccccc1n2C] | 13.02 ± 1.58 |
| CS-X-95 | 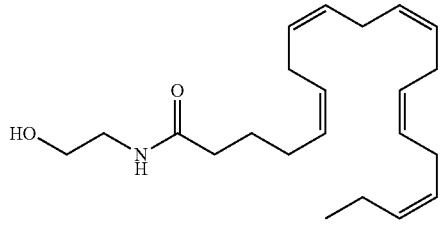 [SMILES: CC/C=C\C/C=C\C/C=C\C/C=C\C/C=C\CCCC(=O)NCCO] | 11.51 ± 0.72 |

TABLE 9-continued

Other exemplary compounds of the invention

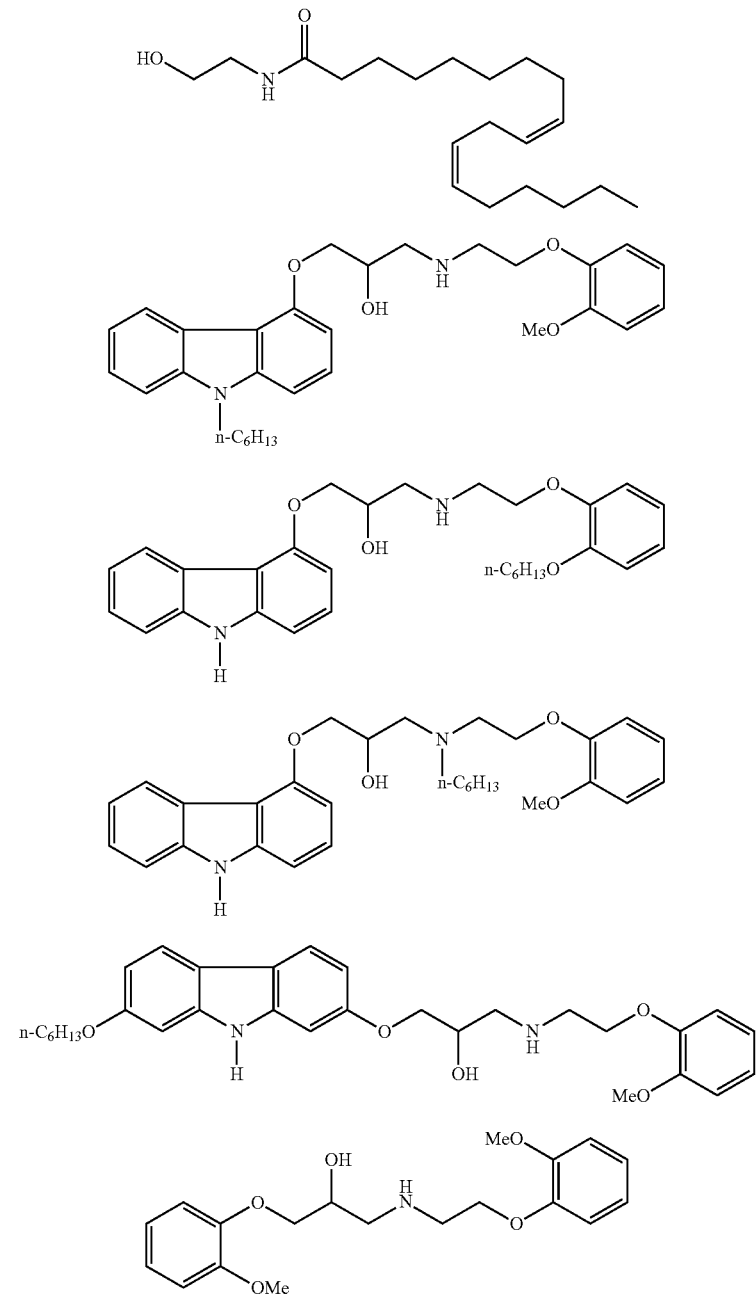

These results demonstrate that considerable variation in the structure of carvedilol is possible while retaining strong SOICR-suppressing activity in the RyR2-R4496C mutant HEK293 single cell assay. As can be seen above, many compounds of the invention showed equal or superior SOICR inhibitory activity compared to carvedilol (1). Thus, significant changes can be tolerated in the catechol, linker and carbazole moieties without loss of activity relative to the clinically useful drug 1. Compounds in Table 1 show significant activity. Beneficial catechol modifications include chlorination of the 4'- and 5'-positions (compound 6), which is expected to block metabolic oxidation at those sites and possibly retard clearance. The 2'-methoxy group can be replaced by H, OH, Me or MeS substituents (compounds 8, 9, 10 and 11) and the 1'-ether oxygen can be replaced by S (compound 12) or $CH_2$ (compounds 13 and 14) without deleterious effects on SOICR inhibition. Remarkably, the simple phenyl derivative 14 is roughly twice as potent as 1. This shows that the compounds in Table 1 or its analogs are good candidates as SOICR inhibitors with diminished α-adrenergic blocking properties, as the latter property is often associated with catechol-containing congeners.

Since the β-amino alcohol functionality has been shown to play a key role in mediating β-adrenergic blockade via multiple hydrogen-bonding interactions with the β-receptor, the alkylation of these key groups via incorporation into cyclic structures or by simple methylation is expected to disrupt β-blockade. Methylation of either the secondary alkylamine or the carbazole nitrogen, or of the hydroxyl group is also expected to suppress β-blockade, and the relatively strong SOICR inhibition of 29-31 offers another potential means for achieving selective SOICR suppression.

The variously homologated analogs in Table 3 (2, 32-34 and 36-38) and the compounds with interposed amino alcohol linkers (39 and 40) all showed strong SOICR suppression in the mutant HEK293 cells. The homologated compound 2 and the analogs 3 and 4 containing 3- and 2-substituted carbazole moieties, respectively, have already been shown to reduce β-blockade of about 1000-fold relative to carvedilol.[32] The other compounds containing homologated, interposed and relocated side chains in Tables 3-5 are promising classes for further investigation as SOICR inhibitors with cleaner pharmacological profiles than carvedilol.

As shown in Table 6, several analogs lacking the carbazole nitrogen or other hydrogen-bonding functionalities showed a relatively strong activity. Thus, the fluorenyl derivative 62, naphthyl derivatives 68 and 69, and the adamantyl analogs 70-72 demonstrate that the hydrogen-bonding carbazole NH functionality that participates in binding to the β-receptor is not required for SOICR inhibition. The more extensive structural modifications to the compounds listed in Table 7 also had varied effects on SOICR suppression. Of special interest are the benzomorpholine derivative 83 and the amides 93 and 94, with $IC_{50}$'s ranging from 3.55 to 5.76 µM, compared to 15.9 µM for 1.

The complete absence of SOICR inhibitory activity in the case of metoprolol (95), the dibromocarbazole derivatives 96 and 97, and the S107 derivatives 99-101 indicates that conventional β-blockers and antiarrhythmic agents in Table 8 express their antiarrhythmic effects through different mechanisms than the active compounds described in Tables 1-7. Only the carvedilol-resembling analog 97 and the thiazepine JTV519 (102) exhibited any measurable effect on SOICR suppression.

Synthesis

The synthesis of compounds 1 and 6-8 and 10-16 in Table 1 was achieved by reacting the commercially available epoxide 103a with the corresponding amines 104a-l, as shown in FIG. 1. Cyclization with chloroacetyl chloride afforded lactams 17-20, while the use of 1,1'-carbonyldiimidazole or dimethyl carbonate afforded products 25-27 in Table 2. The reduction of 17-20 with lithium aluminum hydride provided 21-24. The free phenol 28 was obtained by demethylation of 27 with boron tribromide, while hydrolysis of 28 afforded the amino alcohol 9.

Figure 2:
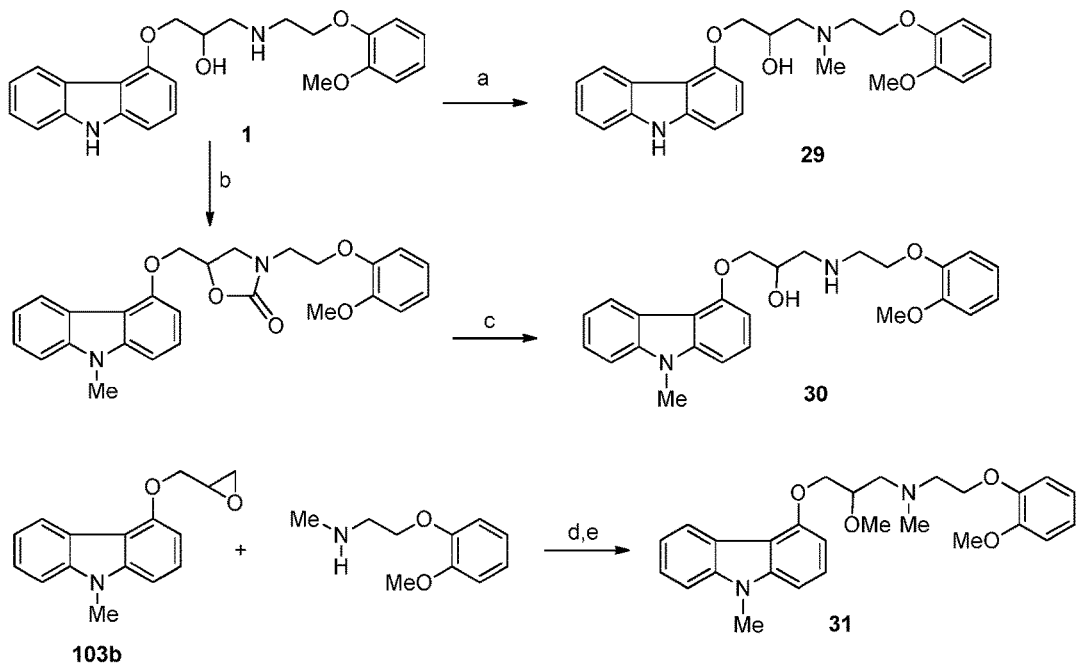

The methylated product 29 in Table 2 was prepared by methylation of 1 with iodomethane, while 30 was obtained from 1 by cyclization and N-methylation with dimethyl carbonate in one step, followed by hydrolysis (FIG. 2). Compound 31 was produced from the reaction of epoxide 103b with the N-methyl derivative of amine 104a, followed by O-methylation with iodomethane.

The products 2 and 33 in Table 3 were prepared from the reactions of amine 104a with the homologated epoxides 105 and 106, in turn obtained from 4-hydroxycarbazole and the corresponding homologated haloepoxides as in the case of 103 in FIG. 1. Alternatively, 34 was produced from 4-hydroxycarbazole and the monotosylate 109. Compounds 36-38 were obtained from epoxide 103a and amines 110 and 111a,b, respectively, while the product 39, containing transposed alcohol and amine functionalities, was prepared from the carbazole derivative 112 and epoxide 113. These processes are summarized in FIG. 3. Cyclizations to afford lactams 32, 35 and 40 were effected from the corresponding amino alcohols with chloroacetyl chloride, as shown previously for 17-20 in FIG. 1.

Figure 5:
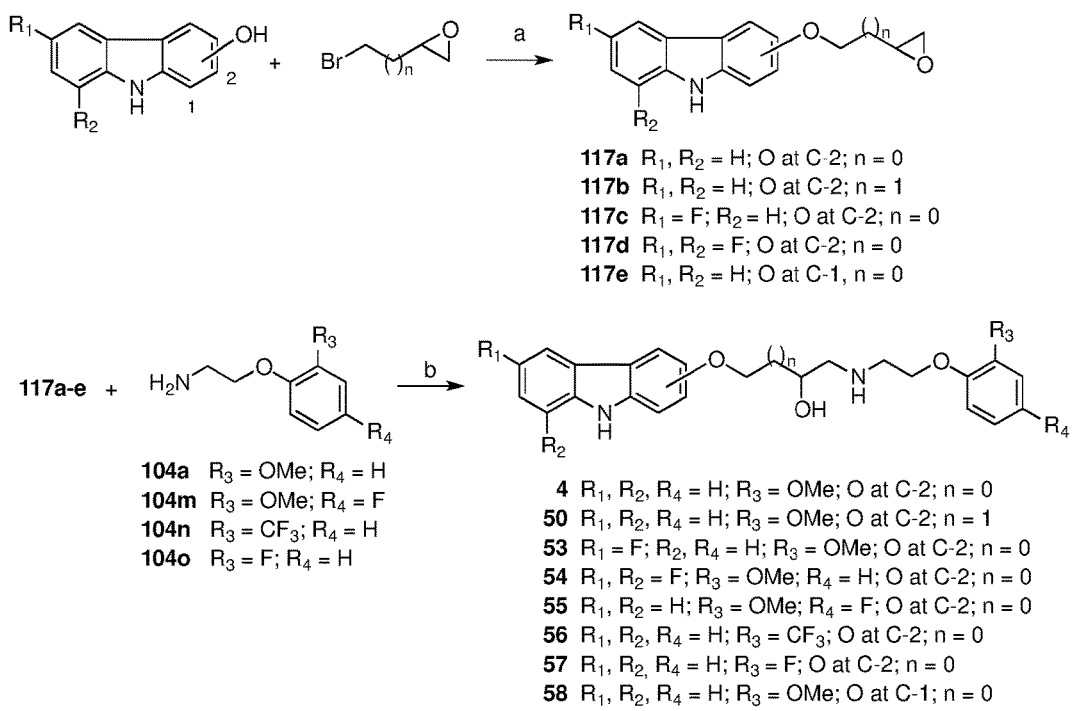
Figure 3:
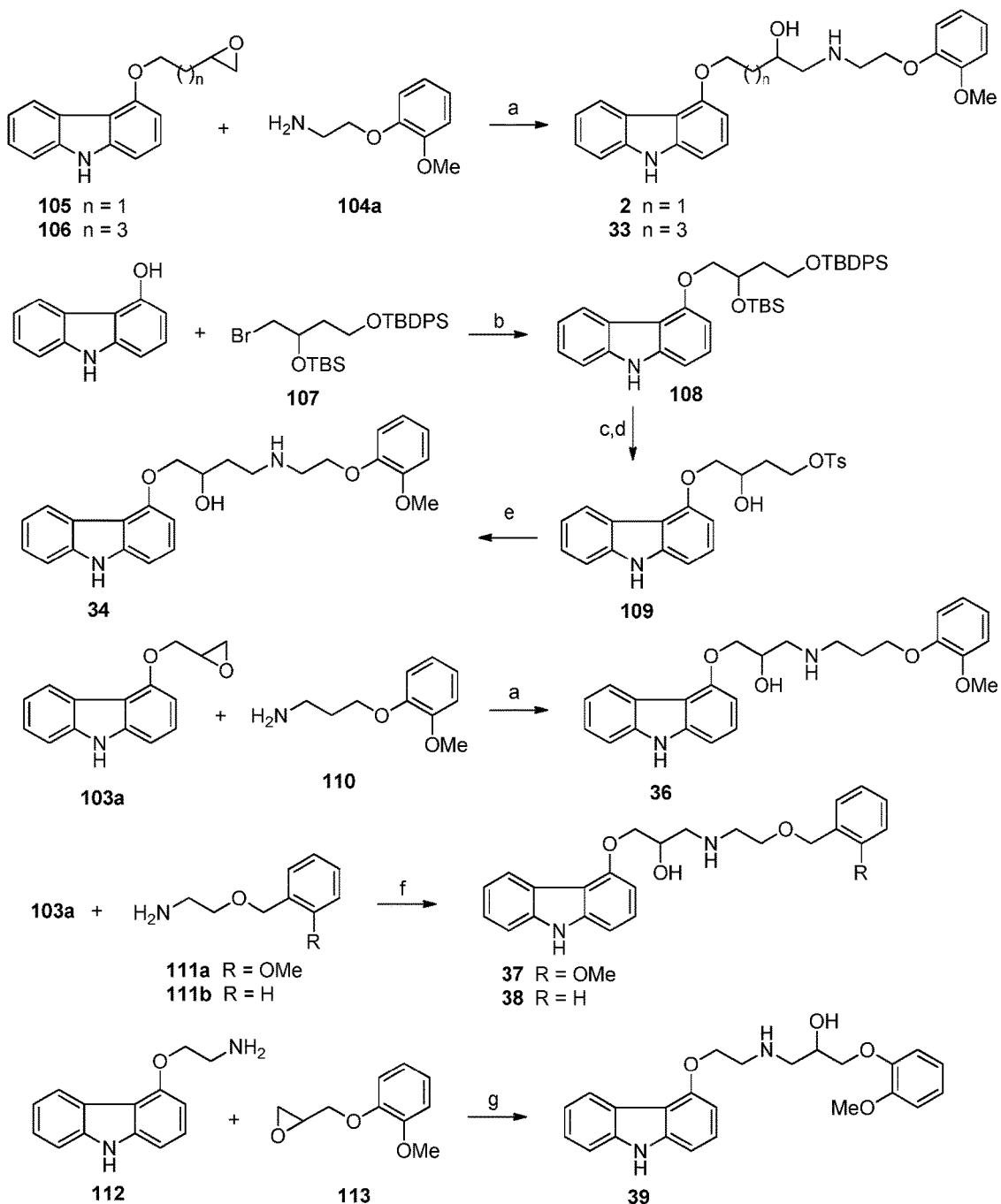
Figure 4:
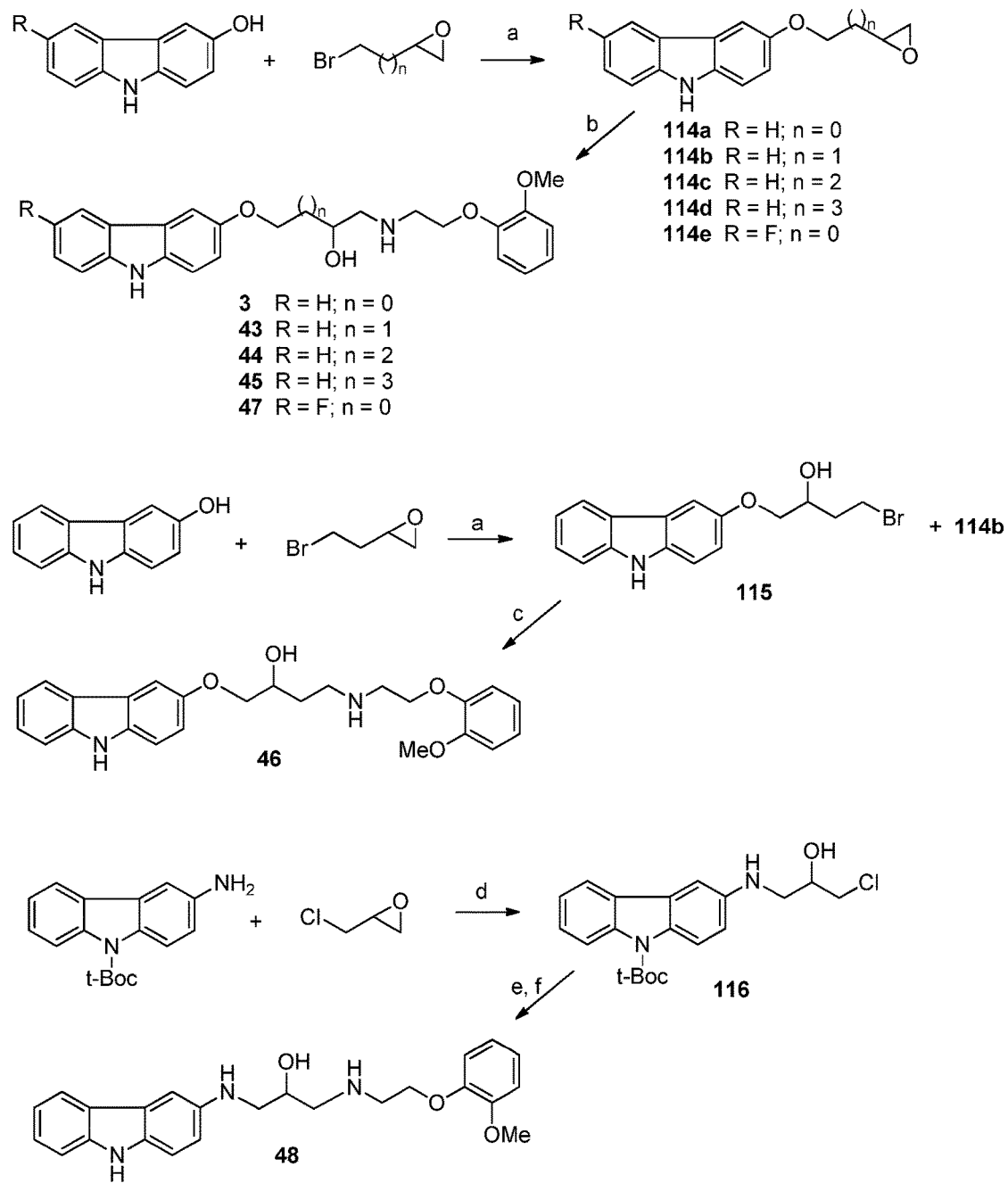

While the products in Tables 1-3 originated from 4-hydroxycarbazole, the syntheses of those in Table 4 were carried out similarly, but employing 3-hydroxycarbazole, its 6-fluoro derivative or 3-aminocarbazole instead, as shown in FIG. 4. Compound 46 was obtained by alkylation of amine 104a with bromide 115, which was obtained as a byproduct in the preparation of epoxide 114b. Similarly, compound 48 was obtained by alkylation of 104a with chloride 116, in turn obtained from 9-t-Boc-protected 3-aminocarbazole and epichlorohydrin. Furthermore, the products in Table 5 were obtained by analogous methods, employing 2-hydroxycarbazole, its 6-fluoro or 6,8-difluoro analogs, or 1-hydroxycarbazole as starting materials (FIG. 5). Lactams 41, 49 and 51 were again obtained by cyclization of the corresponding amino alcohols with chloroacetyl chloride, while cyclizations to afford 42 and 52 were effected with bromomethanesulfonyl chloride or 1,1'-carbonyldiimidazole.

Figure 6:
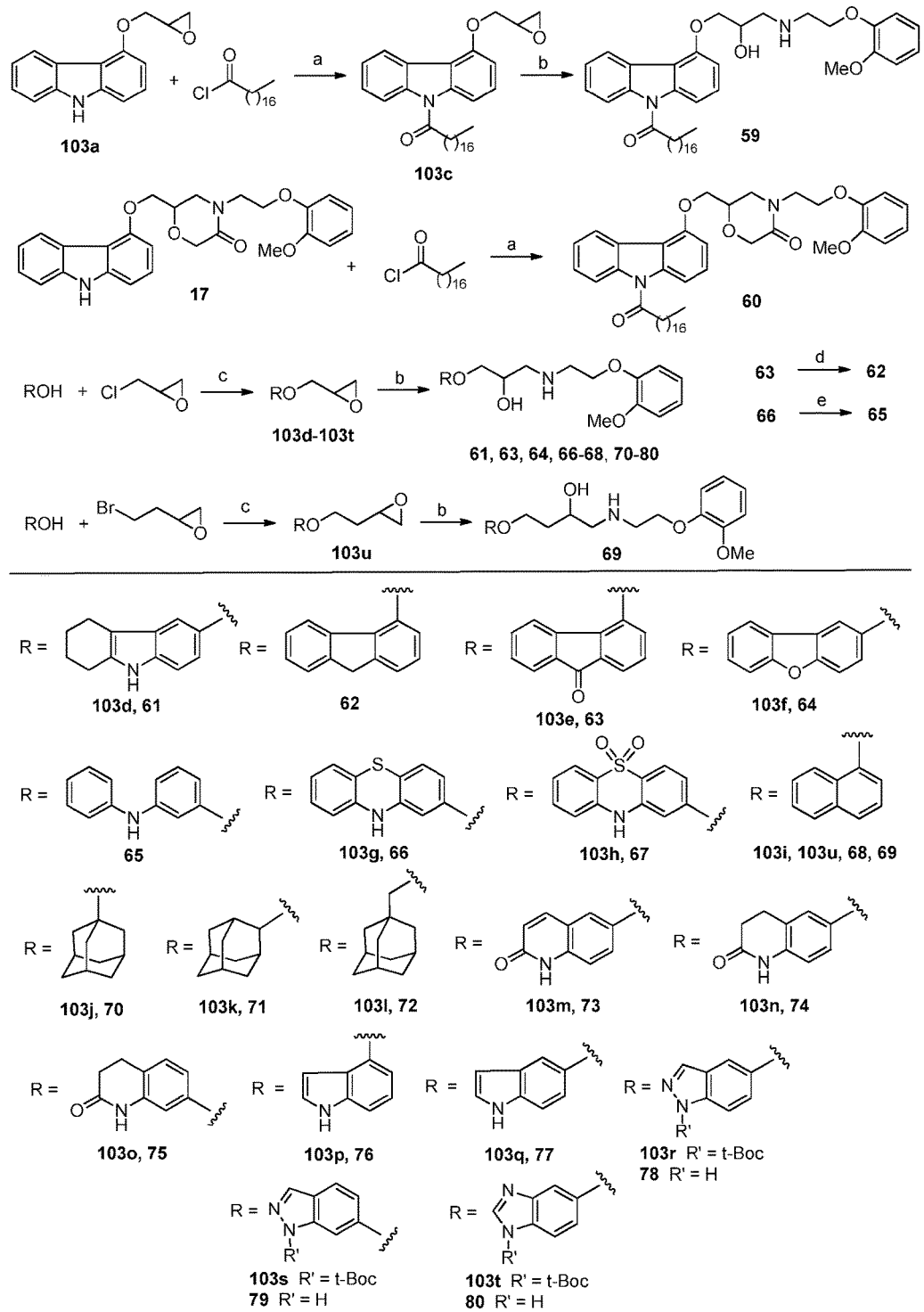

The N-acylated carbazole derivatives 59 and 60 in Table 6 were prepared as shown in FIG. 6. While 60 was prepared by direct acylation of 17, 59 was more easily obtained by prior acylation of epoxide 103a, followed by ring-opening with amine 104a in the usual manner. The other compounds in Table 6 were prepared by alkylating the other indicated phenols or alcohols instead of 4-hydroxycarbazole with the corresponding haloalkyl epoxides, followed by treatment with amine 104a, as indicated in FIG. 6. Product 62 was obtained by Wolff-Kishner reduction of ketone 63, while desulfurization of 66 with nickel boride afforded 65.

Figure 7:
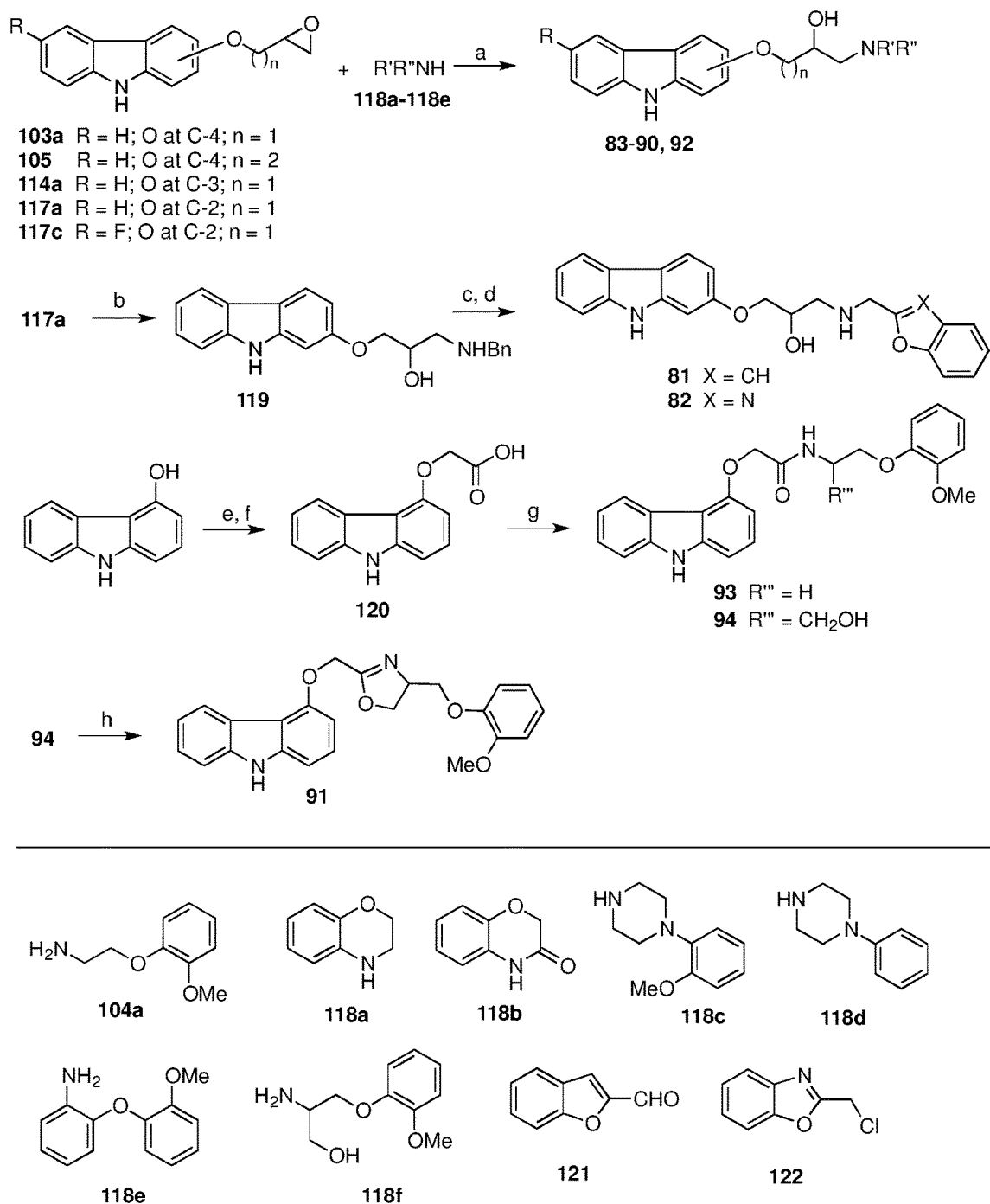

The products 83-90 and 92 in Table 7 were obtained by treating epoxides 103a (entries 3, 4, 9, 10 and 12), 105 (entry 5), 114a (entry 6), 117a (entry 7) or 117c (entry 8) with the corresponding amines 104a or 118a-f, as shown in FIG. 7. The benzofuran and benzoxazole derivatives 81 and 82 (entries 1 and 2) were produced by reductive amination or alkylation of amine 119 with aldehyde 121 or chloride 122, respectively. Amides 93 and 94 (entries 13 and 14) were formed by amidation of carboxylic acid 120 with amines 104a or 118f, respectively, using N-(3-diethylaminopropyl)-N'-ethylcarbodiimide hydrochloride (EDC hydrochloride) and 1-hydroxybenzotriazole hydrate (HOBT·$H_2O$) as coupling reagents. Product 91 (entry 11) was prepared by cyclization of 94 with diethylaminosulfur trifluoride (DAST).

Figure 8:
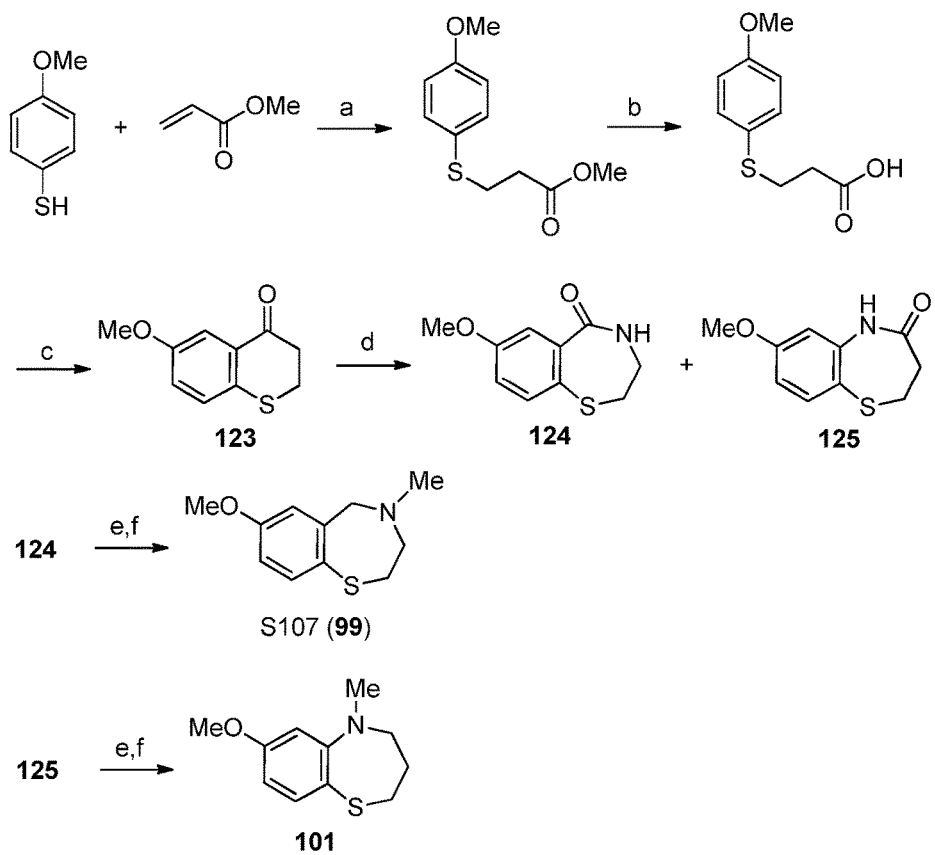

Metoprolol (95) was obtained from commercial sources, while 4,6-dibromo-3-hydroxycarbazole (96) was prepared by a literature procedure. The conversion of 96 to 97 and its further transformation to 98 was achieved via the same procedure that was employed for the preparation of 1 from 4-hydroxycarbazole, and for the cyclization of 1 to 17, as shown in FIG. 1. Products S107 (99) and its hydrochloride salt (100), as well as JTV519 (102) were obtained by known procedures. Alternatively, the regioisomer 101 of S107 was prepared, along with 101, from the known thiapyrone 123, as shown in FIG. 8.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Compounds were prepared as disclosed in U.S. Provisional Patent Application No. 61/872,533, which is incorporated herein by reference in its entirety. Bioassay and in vivo test were also conducted according to the procedures disclosed in U.S. Provisional Patent Application No. 61/872,533.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A compound of the formula:

$$R^1—X^1-L-X^2—R^2$$

wherein
R$^1$ is selected from the group consisting of: carbazol-2-yl; carbazol-3-yl; and carbazol-4-yl, each of which is optionally substituted;
X$^1$ is O;
X$^2$ is O;
R$^2$ is selected from the group consisting of substituted phenyl; substituted benzyl; optionally substituted benzo[d]oxazolyl, and optionally substituted benzofuranyl; and
L is a linker selected from the group consisting of:

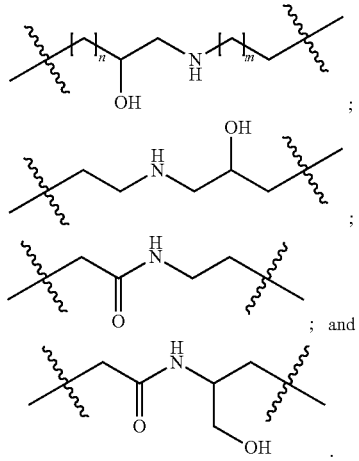

wherein m is 1 or 2; and n is 1 to 4;
provided
when R$^1$ is optionally substituted carbazol-4-yl, then R$^2$ is optionally substituted benzyl;
when R$^1$ is unsubstituted carbazol-3-yl, then linker L has at least 7 backbone atoms in the chain; and
when R$^1$ is unsubstituted carbazol-2-yl, then linker L has at least 7 backbone atoms in the chain, and
R$^2$ is benzo[d]oxazolyl, benzofuranyl, or phenyl substituted with at least one substituent selected from halide and haloalkyl.

2. The compound according to claim 1, wherein R$^1$ is selected from the group consisting of carbazol-3-yl and carbazol-4-yl, each of which is optionally substituted.

3. The compound according to claim 1, wherein L is:

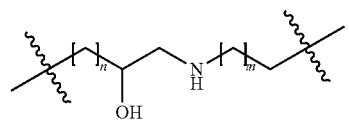

wherein m is 1 or 2; and n is 1 to 4.

4. A method of treating cardiac arrhythmia in a heart failure patient, said method comprising administering to a heart failure patient a therapeutically effective amount of a compound of claim 1 to treat cardiac arrhythmia.

5. The method of claim 4, wherein said compound of claim 1 inhibits store-overload-induced calcium release (SOICR).

6. The method of claim 5, wherein SOICR inhibition of the compound of claim 1 is achieved by regulating calcium efflux through the RyR2 channel.

7. The method of claim 4, wherein calcium ion-induced calcium ion release (CICR) is minimally inhibited or not inhibited.

8. A pharmaceutical composition comprising (i) a compound of claim 1, or a pharmaceutically acceptable salt or a prodrug thereof; and (ii) a pharmaceutically acceptable carrier.

9. The compound according to claim 1, wherein the compound is:

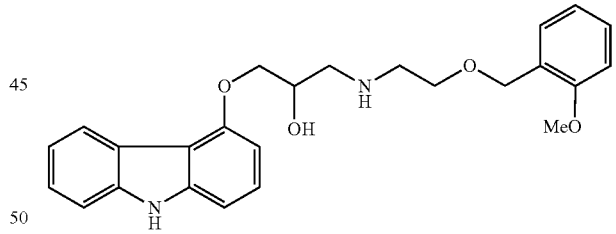

37

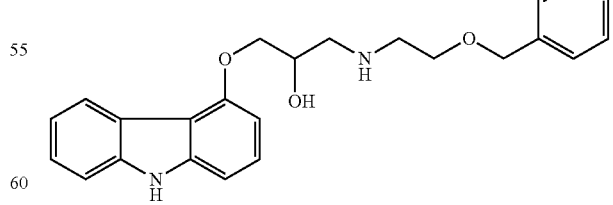

38

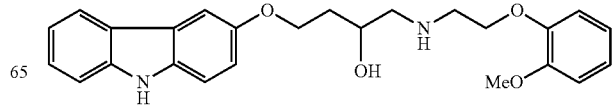

43

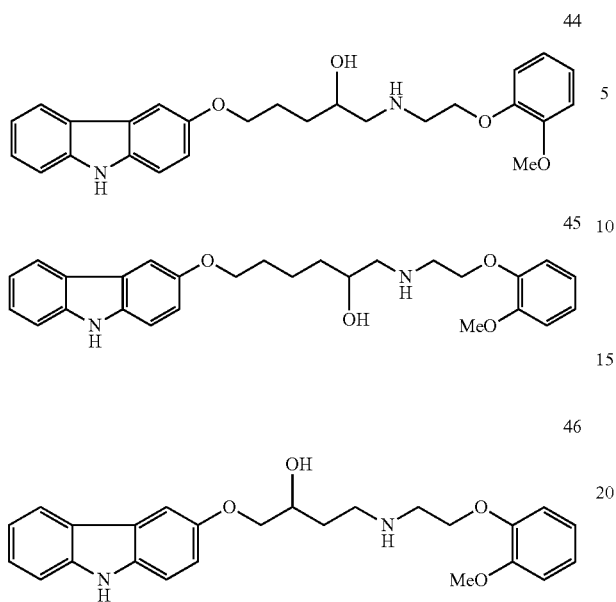
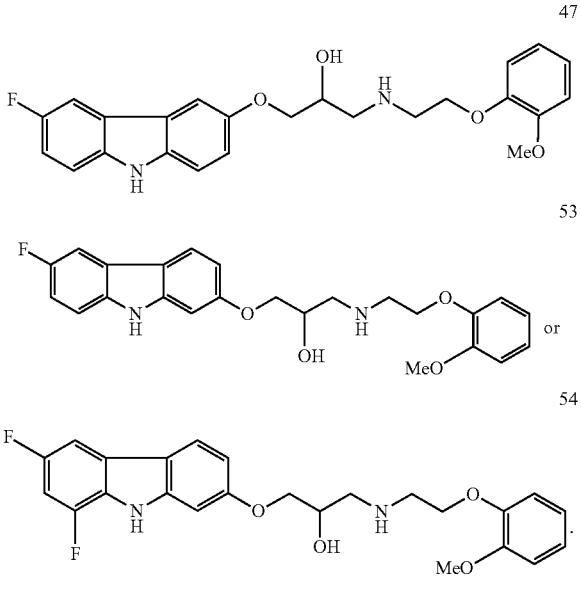
* * * * *